(12) United States Patent
Nelson et al.

(10) Patent No.: US 8,096,302 B2
(45) Date of Patent: Jan. 17, 2012

(54) DEVICES, SYSTEMS, AND METHODS TO FIXATE TISSUE WITHIN THE REGIONS OF THE BODY, SUCH AS THE PHARYNGEAL CONDUIT

(75) Inventors: Lionel M. Nelson, Los Altos, CA (US); Jinfang Liu, Lancaster, PA (US); Ryan P. Boucher, San Francisco, CA (US); Eric N. Doelling, Sunnyvale, CA (US); J. Greg Stine, Longview, TX (US); Lawrence R. Jones, Conifer, CO (US)

(73) Assignee: Koninklijke Philips Electronics N.V. (NL)

( * ) Notice: Subject to any disclaimer, the term of this patent is extended or adjusted under 35 U.S.C. 154(b) by 414 days.

(21) Appl. No.: 11/732,341

(22) Filed: Apr. 3, 2007

(65) Prior Publication Data

US 2007/0186936 A1 Aug. 16, 2007

Related U.S. Application Data

(60) Division of application No. 10/806,372, filed on Mar. 22, 2004, now Pat. No. 7,441,559, which is a continuation-in-part of application No. 10/718,254, filed on Nov. 20, 2003, now Pat. No. 7,360,542, which is a continuation-in-part of application No. 10/656,861, filed on Sep. 6, 2003, now Pat. No. 7,188,627, and a continuation-in-part of application No. 10/236,455, filed on Sep. 6, 2002, now Pat. No. 7,216,648.

(60) Provisional application No. 60/456,164, filed on Mar. 20, 2003, provisional application No. 60/441,639, filed on Jan. 22, 2003.

(51) Int. Cl.
A61F 5/56 (2006.01)
A61F 2/20 (2006.01)

(52) U.S. Cl. ............................ 128/848; 602/902; 623/9
(58) Field of Classification Search ................ 623/2.37, 623/1.11, 1.2, 1.18, 1.35, 1.15, 1.17; 128/848; 602/902; 606/153
See application file for complete search history.

(56) References Cited

U.S. PATENT DOCUMENTS

| | | | |
|---|---|---|---|
| 4,197,840 A * | 4/1980 | Beck et al. | 606/204.25 |
| 4,304,227 A | 12/1981 | Samelson | |
| 4,978,323 A | 12/1990 | Freedman | |
| 5,019,372 A | 5/1991 | Folkman et al. | |
| 5,176,618 A | 1/1993 | Freedman | |
| 5,220,918 A | 6/1993 | Heide et al. | |
| 5,373,859 A | 12/1994 | Forney | |
| 5,465,734 A | 11/1995 | Alvarez et al. | |
| 5,649,540 A | 7/1997 | Alvarez et al. | |
| 5,653,743 A * | 8/1997 | Martin | 623/1.35 |
| 5,792,067 A | 8/1998 | Karell | |
| RE36,120 E | 3/1999 | Karell | |
| 5,988,171 A | 11/1999 | Sohn | |
| 6,231,496 B1 | 5/2001 | Wilk | |
| 6,244,865 B1 | 6/2001 | Nelson et al. | |
| 6,250,307 B1 | 6/2001 | Conrad et al. | |
| 6,390,096 B1 | 5/2002 | Conrad et al. | |
| 6,401,717 B1 | 6/2002 | Conrad et al. | |
| 6,408,851 B1 | 6/2002 | Karell | |
| 6,415,796 B1 | 7/2002 | Conrad et al. | |
| 6,450,169 B1 | 9/2002 | Conrad et al. | |
| 6,490,885 B1 | 12/2002 | Wilkinson | |

(Continued)

*Primary Examiner* — Patricia Bianco
*Assistant Examiner* — Tarla Patel

(57) ABSTRACT

Systems and methods incorporate implant structures, and/or implantation devices, and/or surgical implantation techniques, to make possible the treatment of physiologic conditions, such as sleep disordered breathing, with enhanced effectiveness.

21 Claims, 25 Drawing Sheets

U.S. PATENT DOCUMENTS

| | | |
|---|---|---|
| 6,523,541 B2 | 2/2003 | Knudson |
| 6,636,767 B1 | 10/2003 | Knudson et al. |
| 6,742,524 B2 | 6/2004 | Knudson et al. |
| 6,955,172 B2 | 10/2005 | Nelson et al. |
| 7,073,505 B2 | 7/2006 | Nelson et al. |
| 7,077,143 B2 | 7/2006 | Knudson et al. |
| 7,077,144 B2 | 7/2006 | Knudson et al. |
| 7,146,981 B2 * | 12/2006 | Knudson et al. ............... 128/848 |
| 7,188,627 B2 * | 3/2007 | Nelson et al. ................. 128/898 |
| 2001/0037133 A1 * | 11/2001 | Knudson et al. ................ 607/42 |
| 2001/0047805 A1 | 12/2001 | Scarberry et al. |
| 2002/0151913 A1 * | 10/2002 | Berg et al. ..................... 606/153 |
| 2004/0112390 A1 | 6/2004 | Brooks et al. |
| 2005/0092332 A1 | 5/2005 | Conrad et al. |

* cited by examiner

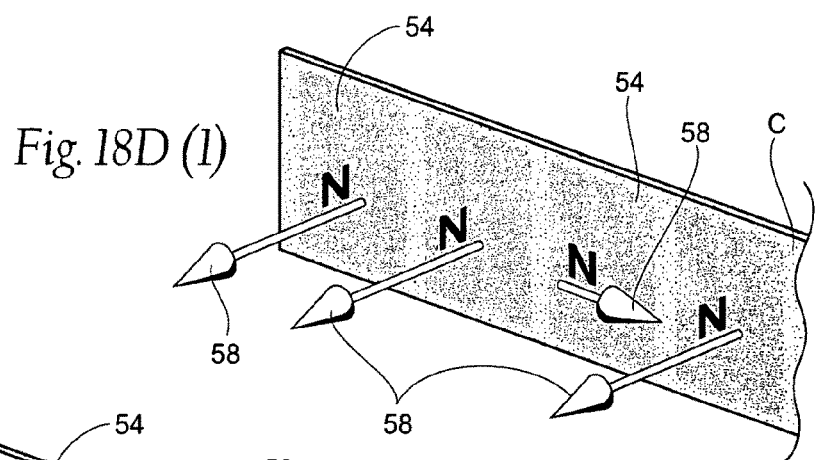
Fig. 18D (1)
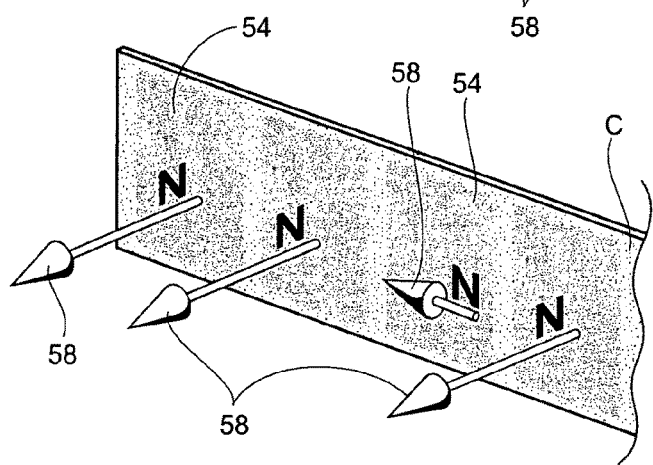
Fig. 18D (2)
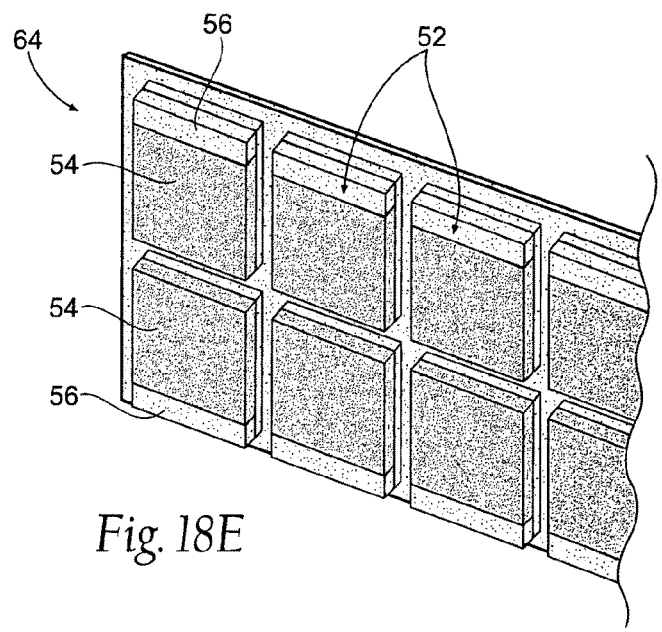
Fig. 18E

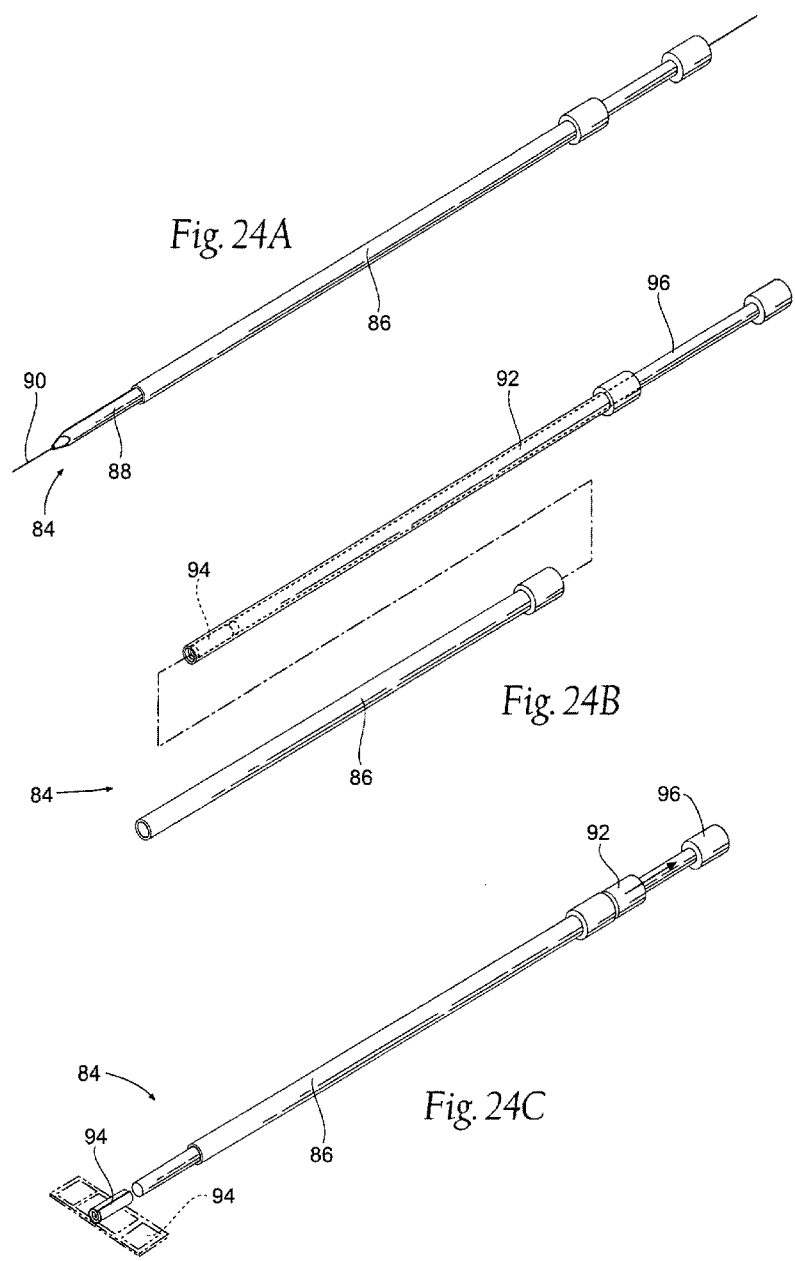

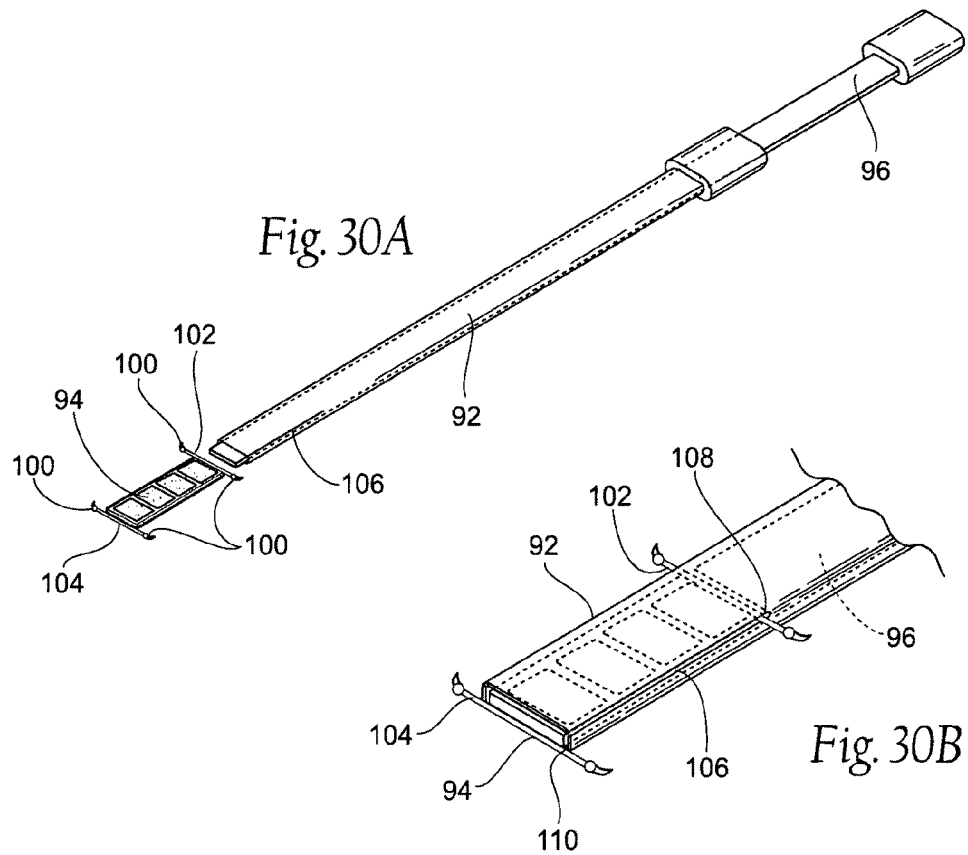
Fig. 30A
Fig. 30B
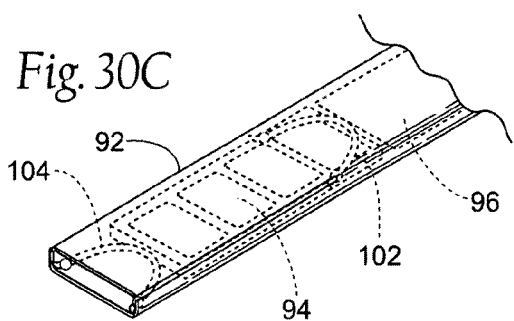
Fig. 30C
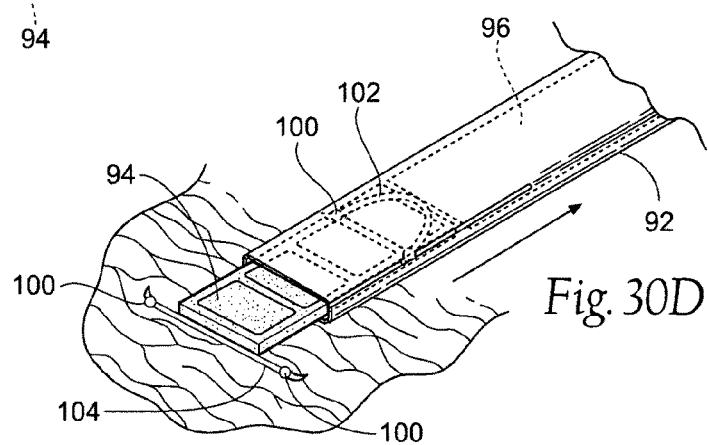
Fig. 30D

DEVICES, SYSTEMS, AND METHODS TO FIXATE TISSUE WITHIN THE REGIONS OF THE BODY, SUCH AS THE PHARYNGEAL CONDUIT

RELATED APPLICATIONS

This application is a divisional of U.S. patent application Ser. No. 10/806,372, filed Mar. 22, 2004, now U.S. Pat. No. 7,441,559, entitled "Devices, Systems, and Methods to Fixate Tissue Within the Regions of the Body, Such as the Pharyngeal Conduit," which is a continuation-in-part of U.S. patent application Ser. No. 10/718,254, filed Nov. 20, 2003, now U.S. Pat. No. 7,360,542, entitled "Devices, Systems, and Methods to Fixate Tissue Within the Regions of the Body, Such as the Pharyngeal Conduit," which is a continuation-in-part of U.S. patent application Ser. No. 10/656,861, filed Sep. 6, 2003, now U.S. Pat. No. 7,188,627, entitled "Magnetic Force Devices, Systems, and Methods for Resisting Tissue Collapse within the Pharyngeal Conduit," which claims the benefit of U.S. Provisional Patent Application Ser. No. 60/441,639, filed Jan. 22, 2003, and U.S. Provisional Patent Application Ser. No. 60/456,164, filed Mar. 20, 2003, which are each incorporated herein by reference. This application is also a continuation-in-part of U.S. patent application Ser. No. 10/236,455, filed Sep. 6, 2002, now U.S. Pat. No. 7,216,648, and entitled "System and Method for Moving and/or Restraining Tissue in the Upper Respiratory System," which is also incorporated herein by reference.

FIELD OF THE INVENTION

The invention is directed to devices, systems, and methods that fixate or brace tissue in targeted body regions, e.g., in the pharyngeal conduit for the treatment of sleep disordered breathing including obstructive sleep apnea.

BACKGROUND OF THE INVENTION

I. The Characteristics of Sleep Apnea

First described in 1965, sleep apnea is a breathing disorder characterized by brief interruptions (10 seconds or more) of breathing during sleep. Sleep apnea is a common but serious, potentially life-threatening condition, affecting as many as 18 million Americans.

There are two types of sleep apnea: central and obstructive. Central sleep apnea, which is relatively rare, occurs when the brain fails to send the appropriate signal to the breathing muscles to initiate respirations, e.g., as a result of brain stem injury or damage. Mechanical ventilation is the only treatment available to ensure continued breathing.

Obstructive sleep apnea (OSA) is far more common. It is one of the several entities that make up the broader group of sleep disordered breathing (SDB). This group of disorders ranges from habitual snoring to OSA. Normally, the muscles of the upper part of the throat keep the airway open to permit air flow into the lungs. When the muscles of the upper airway relax and sag, the relaxed tissues may vibrate as air flows past the tissues during breathing, resulting in snoring. Snoring affects about half of men and 25 percent of women—most of whom are age 50 or older.

In more serious cases, the airway becomes blocked, making breathing labored and noisy, or even stopping it altogether. In a given night, the number of involuntary breathing pauses or "apneic events" can be quite frequent. These breathing pauses are almost always accompanied by snoring between apnea episodes, although not everyone who snores has OSA.

Lack of air intake into the lungs results in lower levels of oxygen and increased levels of carbon dioxide in the blood. The altered levels of oxygen and carbon dioxide alert the brain to resume breathing and cause arousal. The frequent interruptions of deep, restorative sleep often lead to early morning headaches, excessive daytime sleepiness, depression, irritability, and learning and memory difficulties.

The medical community has become aware of the increased incidence of heart attacks, hypertension and strokes in people with moderate or severe obstructive sleep apnea. It is estimated that up to 50 percent of sleep apnea patients have high blood pressure.

Upon an apneic event, the sleeping person is unable to continue normal respiratory function and the level of oxygen saturation in the blood is reduced. The brain will sense the condition and cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep and associated daytime fatigue.

Although some apneic events are normal in all humans, the frequency of blockages will determine the seriousness of the disease and opportunity for health damage. When the incidence of blockage is frequent, corrective action should be taken.

II. Sleep and the Anatomy of the Upper Airway

As FIGS. 1A and 1B show, the upper airway consists of a conduit that begins at the nasal valve, situated in the tip of the nose, and extends to the larynx. Although all tissue along this conduit is dynamic and responsive to the respiratory cycle, only the pharyngeal conduit structures—the tissues in the region of the airway that starts behind the nasal cavity and ends in its connections to the supraglottic larynx—is totally collapsible. The pharyngeal structures and individual anatomic components within this region include the pharyngeal walls; the base of the tongue; the vallecula; the hyoid bone and its attachments; the soft palate with uvula, the palatine tonsils with associated pillar tissue; and the epiglottis.

The cross sectional area of the upper airway varies with the phases of the respiratory cycle. At the initiation of inspiration (Phase I), the airway begins to dilate and then to remain relatively constant through the remainder of inspiration (Phase II). At the onset of expiration (Phase III) the airway begins to enlarge, reaching maximum diameter and then diminishing in size so that at the end of expiration (Phase IV), it is at its narrowest, corresponding to the time when the upper airway dilator muscles are least active, and positive intraluminal pressure is lowest. The upper airway, therefore, has the greatest potential for collapse and closure at end-expiration. Schwab R J, Goldberg A N. *Upper Airway Assessment: Radiographic and other Imaging Techniques. Otolaryngol Clin North Am* 1998; 31:931-968.

Sleep is characterized by a reduction in upper airway dilator muscle activity. For the individual with obstructive sleep apnea (OSA) and perhaps the other disorders which comprise much of the group of entities called obstructive sleep-disordered breathing (SDB), it is believed that this change in muscle function causes pharyngeal narrowing and collapse. Two possible etiologies for this phenomenon in OSA patients have been theorized. One is that these individuals reduce the airway dilator muscle tone more than non-apneics during sleep (the neural theory). The other is that all individuals experience the same reduction in dilator activity in sleep, but that the apneic has a pharynx that is structurally less stable (the anatomic theory). Both theories may in fact be contributors to OSA, but current studies seem to support that OSA patients have an intrinsically structurally narrowed and more collapsible pharynx. Isono S. Remmers J, Tanaka A Sho Y, Sato J, Nishino T. *Anatomy of Pharynx in Patients with Obstructive Sleep Apnea and in Normal Subjects. J Appl Physiol* 1997: 82:1319-1326.

Although anatomic closure is often accentuated at specific sites, such as the velopharyngeal level [Isono, Ibid], studies of closing pressures [Isono, Ibid] supports dynamic fast MRI imaging that shows narrowing and collapse usually occurs along the entire length of the pharynx. Shellock F G, Schatz C J, Julien P, Silverman. J M, Steinberg F, Foo T K F, Hopp M L, Westbrook P R. *Occlusion and Narrowing of the Pharyngeal Airway in Obstructive Sleep Apnea: Evaluation by Ultrafast Spoiled GRASS MR Imaging. Am J of Roentgenology* 1992:158:1019-1024.

III. Prior Treatment Modalities

To date, the only modality that addresses collapse along the entire upper airway is mechanical positive pressure breathing devices, such as continuous positive airway pressure (CPAP) machines. All other modalities, such as various surgical procedures and oral appliances, by their nature, address specific sectors of the airway (such as palate, tongue base and hyoid-vallecula levels), but leave portions of pharyngeal wall untreated. This may account for the considerably higher success rate of CPAP over surgery and appliances in controlling OSA. Although CPAP, which in essence acts as an airway splint for the respiratory cycle, is highly successful, it has some very significant shortcomings. It can be cumbersome to wear and travel with, difficult to accept on a social level, and not tolerated by many (for reasons such as claustrophobia, facial and nasal mask pressure sores, airway irritation). These factors have lead to a relatively poor long-term compliance rate. One study has shown that 65% of patients abandon their CPAP treatment in 6 months.

The need remains for simple, cost-effective devices, systems, and methods for reducing or preventing sleep disordered breathing events.

SUMMARY OF THE INVENTION

One aspect of the invention provides systems and methods that include implant structures, and/or implantation devices, and/or surgical implantation techniques, which make possible the treatment of physiologic conditions with enhanced effectiveness.

In one embodiment, the systems and methods provide an implant comprising a structure sized and configured to occupy a targeted tissue region in an oral cavity. The implant includes at least one member carried by the structure that is sized and configured to be selectively deployed outward of the structure into contact with tissue. The at least one member can serve, e.g., to anchor the structure in tissue, or to fixate the structure in tissue.

In one arrangement, the at least one member can be resiliently biased toward a deployed condition outward of the structure. In the arrangement, the at least one member can be resiliently movable within a delivery tool toward an inboard condition generally along the structure. In this arrangement, the at least one member resiliently returns toward the deployed condition upon release from the delivery tool.

In one arrangement, the at least one member comprises an arm that is deflectable between an inboard condition extending generally along the structure and an outboard condition extending outward of the structure in contact with tissue. The arm can comprise, e.g., an elastic material, or a shape memory material, or a material having a spring-like mechanical property. The arm, e.g., can be resiliently biased toward the outboard condition.

In one arrangement, the implant can include a plurality of members, each sized and configured to be selectively deployed outward of the structure into contact with tissue. At least some of the plurality of members can be disposed in a same region of the structure, e.g., an end region of the structure. At least some of the plurality of members can be disposed in different regions of the structurem, e.g., in opposite ends of the structure or on opposite sides of the structure.

Another aspect of the invention provides an implant system comprising an implant and a delivery tool for the implant. The implant is sized and configured to occupy a targeted tissue region in an oral cavity. The implant includes at least one member carried by the implant that is deflectable between an inboard condition extending generally along the structure and an outboard condition extending outward of the structure in contact with tissue. The at least one member is resiliently biased toward the outboard condition. According to this aspect of the invention, the delivery tool is sized and configured to hold the implant and deflect the at least one member toward the inboard condition for delivery to the targeted tissue region. The delivery tool is also sized and configured to selectively release the implant within the targeted tissue region, to free the at least one member to resiliently deflect toward the outboard condition in contact with tissue 23. When deflected in the outboard condition, the at least one member can serve to anchor the implant in tissue, or to fixate the implant in tissue.

Another aspect of the invention provides a method. The method includes providing an implant sized and configured to occupy a targeted tissue region in an oral cavity. The implant includes at least one member carried by the implant that is deflectable between an inboard condition extending generally along the structure and an outboard condition extending outward of the structure in contact with tissue. The at least one member is resiliently biased toward the outboard condition. The method further includes delivering the implant to a targeted tissue region in an oral cavity with the at least one member deflected toward the inboard condition. The method further includes allowing the at least one member to resiliently deflect toward the outboard condition in contact with tissue in the tissue region. When deflected in the outboard condition, the at least one member can serve to anchor the implant in tissue, or can serve to fixate the implant in tissue.

The systems and methods can serve to stabilize a desired orientation of the tissue region by providing the implant as described, delivering the implant, and allowing the at least one member to resiliently deflect toward the outboard condition to stabilize the implant in the tissue region. By stabilizing a desired orientation of the tissue region, sleep disordered breathing can be treated using the implant.

The systems and methods can also provide at least one tool and/or instructions for placing the implant in a tissue region, e.g., through a percutaneous access path; or by forming a surgical flap; or by forming a surgical pocket. The systems and methods can also include providing at least one tool and/or instructions for stabilizing the implant within a mucosa, or a submucosa, or against a fascia, or against or within a muscle; or, alternatively, the tool and/or instructions can make possible the stabilization of the implant against a submucosa, or a fascia, or against or within a muscle, without stabilizing through a mucosa. The systems and methods can include other tools and instructions, e.g., to make various mechanical fixation materials for the implant accessible; or to make agents that stimulate rapid fibrosis in the implantation site available; or to provide antibiotic materials for the implantation site. The systems and methods can comprise the components individually or as an assembled kit. The various instructions can be in written form, electronic form, or verbal form, which can be provided in the kit and/or as part of a training program or web site for clinicians.

The systems and methods can be used, e.g., to treat airway collapse and increased airway resistance associated with the entire spectrum of obstructive sleep-disordered breathing. The systems and methods can also be used to lend upper airway support in neurological associated dystonic disorders.

Other features and advantages of the invention shall be apparent based upon the accompanying description, drawings, and claims.

DESCRIPTION OF THE DRAWINGS

FIGS. 18D(1) and 18D(2) are perspective front views of an alternative embodiments of stabilized magnetic structures that can be used in the magnetic force system shown in FIG. 2, the structures including an array of permanent magnet cores mounted on a flexible carrier, with the pole of at least one of the magnet cores reoriented by ninety degrees relative to its neighboring cores.

FIG. 18E is a perspective front view of an alternative embodiment of stabilized magnetic structure that can be used in the magnetic force system shown in FIG. 2, the structure including an array of stabilized magnetic assemblies shown in FIG. 18B mounted in two rows on a flexible carrier.

FIGS. 24A, 24B, and 24C show an instrument system for percutaneously implanting an implant comprising a cylindrical access cannula through which a correspondingly-shaped tissue dissection tool and implant delivery tool can be passed, FIG. 24A showing passage of the tissue dissection tool through the cannula, FIG. 24B showing the passage of the implant delivery tool through the cannula, and FIG. 24C showing the delivery of the implant by the implant delivery tool.

FIGS. 30A, 30B, 30C, and 30D are perspective views of an implant and associated delivery tool, the implant having integrated tissue stabilization elements, which are automatically deployed into tissue as the implant is expelled from the delivery tool, FIG. 30A showing the outboard configuration of the implant stabilization elements after the implant has been completely expelled from the tool, FIGS. 30B and 30C showing the loading of the implant into the tool, during which the stabilization elements are bent toward a low profile inboard configuration, and FIG. 30D showing the deployment of the stabilization elements as the implant is being expelled from the tool.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. Magnetic Force Systems to Fixate or Brace Tissue

A. Overview

Figure 1:
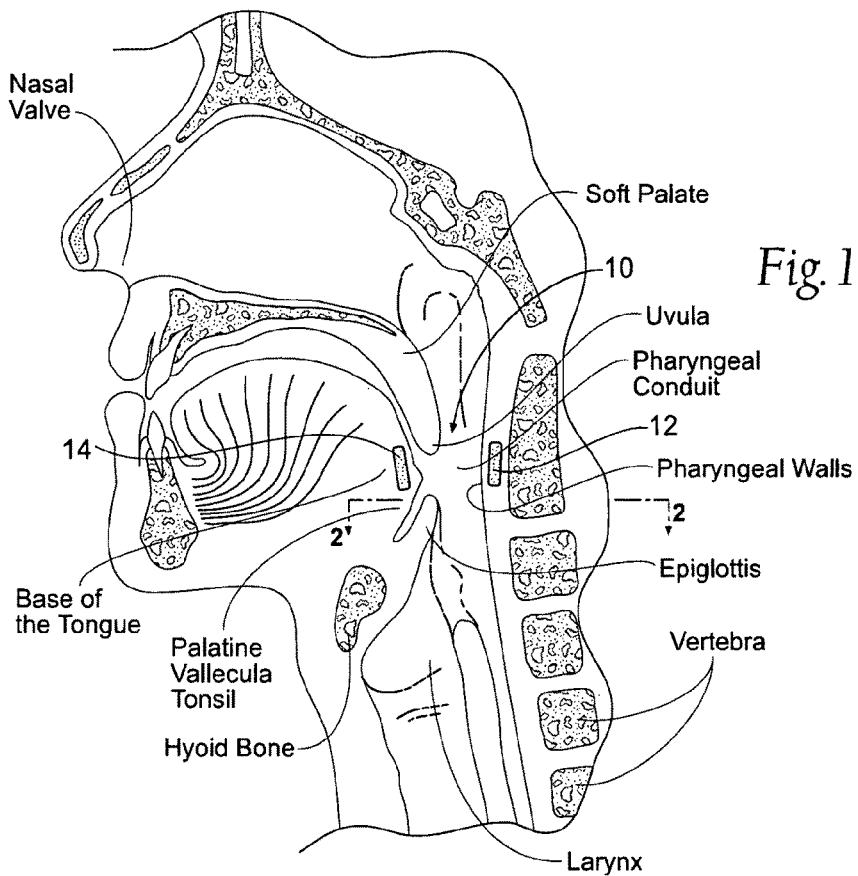
FIG. 1 is an anatomic view of the upper airway in a human, showing certain pharyngeal structures and individual anatomic components within the pharyngeal conduit, and the showing the installation of a magnetic force system in the tongue and pharyngeal wall.
Figure 2:
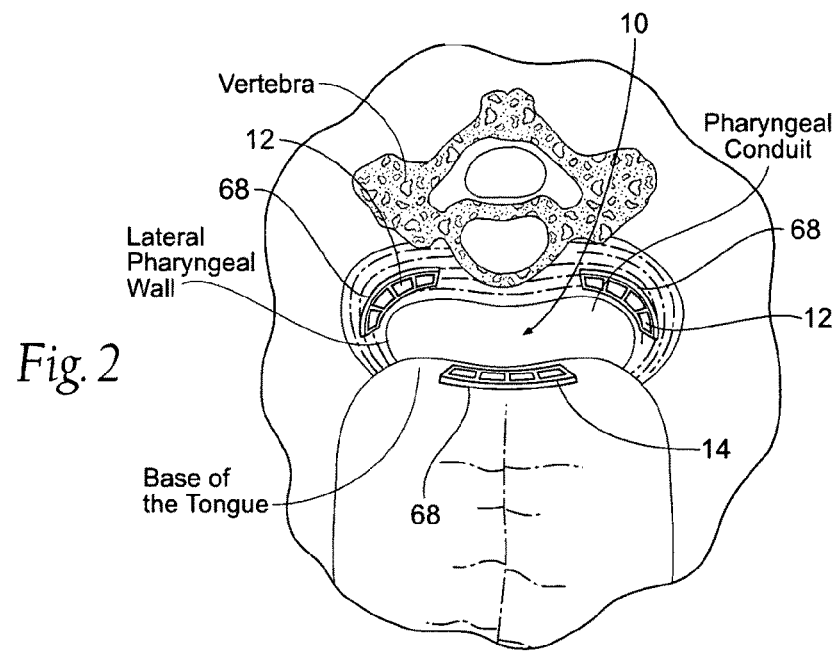
FIG. 2 is a superior anatomic view taken generally along line 2-2 in FIG. 1, showing the magnetic force system shown in FIG. 1, which, in use, fixates or braces tissue in that targeted body region.

FIGS. 1 and 2 show a magnetic force system 10 that, in use, fixates or braces tissue in a targeted body region. In FIGS. 1 and 2, the targeted body region comprises pharyngeal structures and individual anatomic components within the pharyngeal conduit. The targeted pharyngeal structures and individual anatomic components within this region can include the pharyngeal walls; the base of the tongue; the vallecula; the soft palate with uvula; the palatine tonsils with associated pillar tissue; and the epiglottis. These anatomic regions are shown in FIG. 1.

In the particular embodiment illustrated (see FIG. 2), the magnet force system 10 includes one or more ferromagnetic structures 12 implanted in the pharyngeal wall and/or one or more ferromagnetic structures 14 implanted in the posterior of the tongue. Both ferromagnetic structures 12 and 14 comprise at least one permanent magnet. Examples of known permanent magnet materials include alloys of Neodymium-Iron-Boron (NdFeB), alloys of Aluminum-Nickel-Cobalt (AlNiCo), and Samarium Cobalt (SmCo). The permanent magnets can be magnetized through the thickness in a variety of modes, such as multipole faces, radial homopolar, axial, or diametrical.

The permanent magnets in the opposing structures 12 and 14 possess the same magnetic orientation (North-North or South-South). According to physical laws, poles of like polarity repel each other with a magnetic force. The force of magnetic repulsion depends on the strength of the magnets and the distance between the poles.

The repelling force between the opposing tongue magnet(s) and pharyngeal wall magnet(s) is selected to be of a strength sufficient to remodel native tissue conditions within the airway. The repelling force alters existing morphology and/or motility and/or shape of tissue that, if not altered, could lead to tissue collapse, particularly during the respiratory cycle. The implanted ferromagnetic structures 12 and 14 establish tissue conditions that fixate or brace the tissue, to resist collapse along the pharyngeal conduit when imminent, i.e., during sleep, but without significantly stiffening the native tissue at times when tissue collapse is not imminent.

The orientation of the structures 12 and 14 can vary. The structures 12 and 14 may be oriented within tissue horizontally (as shown in FIG. 2), and/or vertically (see, e.g., FIGS. 23C and 26B), and/or diagonally, and/or in intermediate orientations (e.g., sloped), and/or combinations thereof.

It should be appreciated that one of the structures 12 and 14 can be located external of the pharyngeal conduit, to magnetically interact with a structure implanted within the pharyngeal conduit. The magnetic force field created may be attracting and/or repelling, depending upon the anatomic orientation of the structures and the physiologic outcome desired. Various embodiments of magnetic force systems using implanted and/or external magnetic structures are shown in U.S. patent application Ser. No. 10/656,861, filed Sep. 6, 2003 and entitled "Magnetic Force Devices, Systems, and Methods for Resisting Tissue Collapse within the Pharaygeal Conduit," which is incorporated hereby by reference.

The system 10 can be used to treat airway collapse and increased airway resistance associated with the entire spectrum of obstructive sleep-disordered breathing. The system 10 can also be used to lend upper airway support in neurological associated dystonic disorders. The system 10 can also be used in other regions of the body where tissue remodeling and/or bracing is indicated.

The fixation or bracing function of the implanted structures 12 and 14 impart improved comfort, tolerance, and bio-acceptance to the implanted structures 12 and 14 for the patient. The fixation or bracing function is achieved without indiscriminate dampening (i.e., stiffening) the spring constant of native tissue in the pharyngeal conduit (which is not desirable). The fixation or bracing function is achieved due to the controlled application of static and/or kinetic forces that push or pull on tissue, without themselves imparting stiffness to the tissue in the pharyngeal conduit. The size and configuration of the implanted structures are selected with the ease and bio-comfort of implantation in mind, while at the same time providing sufficient static and/or kinetic forces to resist tissue collapse when collapse is imminent, taking into account the anatomy of the region of implantation and orientation of other components of the system 10. The implanted structures 12 and 14 thereby provide conformability, tolerance, and comfort for the patient, without significantly dampening the spring constant of native tissue.

B. Magnetic Arrays

The implanted ferromagnetic structures 12 and/or 14 can each comprise a single or discrete source of magnetism having a given desired orientation. For example, a single permanent magnet, comprising a body of a ferromagnetic material, can comprise a single source of magnetism having a given orientation.

A given implanted ferromagnetic structure 12/14 of whatever form or configuration can be coated, plated, encapsulated, or deposited with a selected protective material 68 (see FIG. 2). The protective material 68 is selected to provide a corrosion resistant and biocompatible interface, to prevent interaction between the structure and tissues/fluids of the body. The protective material 68 is also desirably selected to form a durable tissue interface, to provide longevity to the structure, and thereby provide resistance to structural fatigue and/or failure. The protective material 68 can be selected among various types of materials known to provide the desired biocompatibility, resistance to corrosion, and durability. For example, the protective material 68 can comprise gold, and/or silver, and/or titanium material plated, deposited, or otherwise coated upon the structure. As another example, the protective material 62 can comprise a parylene coating. As other examples, the protective material 68 can comprise a silicone polymer, a non-toxic epoxy, a medical grade polyurethane, or a U.V. curable medical acrylic co-polymer.

The protective material 68 may also incorporate anticoagulants and/or antibiotics, be antimicrobial in nature, or be treated to create an antimicrobial surface.

1. Discrete Permanent Magnets on a Flexible Carrier

Figure 3:
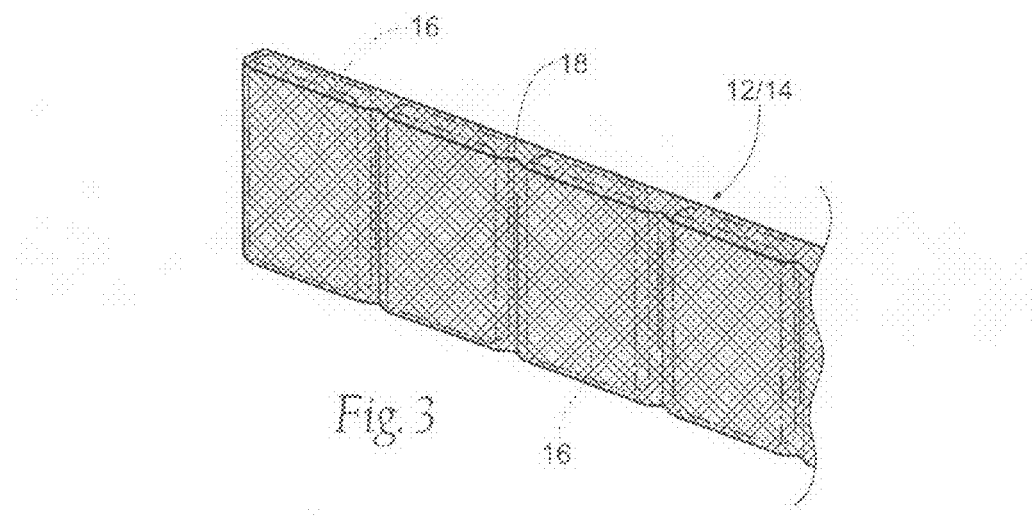
FIG. 3 is a perspective front view of a magnetic structure that can be used in the magnetic force system shown in FIG. 2, the structure including an array of permanent magnets mounted on a flexible carrier.

As shown in FIG. 3, the ferromagnetic structures 12 and/or 14 can each comprise a flexible or compliant array of discrete permanent magnets 16, carried as a unit on a support carrier 18, or otherwise directly linked together. The support carrier 18 is desirably made from a material that imparts biocompatibility, durability, and flexibility to the magnetic array. The carrier 40 may be made, e.g., of a flexible or semi-rigid material such as polycarbonate, silicone rubber, polyurethane, hydrogel, etc, or a flexible or semi-rigid plastic and/or metal and/or fabric and/or textile and/or ceramic material.

The material of the carrier 18 can enclose the magnets 16, or the magnets 16 can be carried on the surface of the carrier 18. The spacing between the magnets 16 on or within the carrier 18 provides the requisite flexibility desired. The individual magnets 16 can have various geometries—rectangular, cylindrical, spherical, oval, etc.—as long as the desired physiologic response is achieved.

Further details of flexible magnetic arrays of the type described can be found in copending U.S. patent application Ser. No. 10/236,455, filed Sep. 6, 2002 and entitled "Systems and Methods for Moving and/or Restraining Tissue in the Upper Respiratory System," which is incorporated herein by reference.

2. Polymer-Bonded Magnetic Structures

Figure 4:
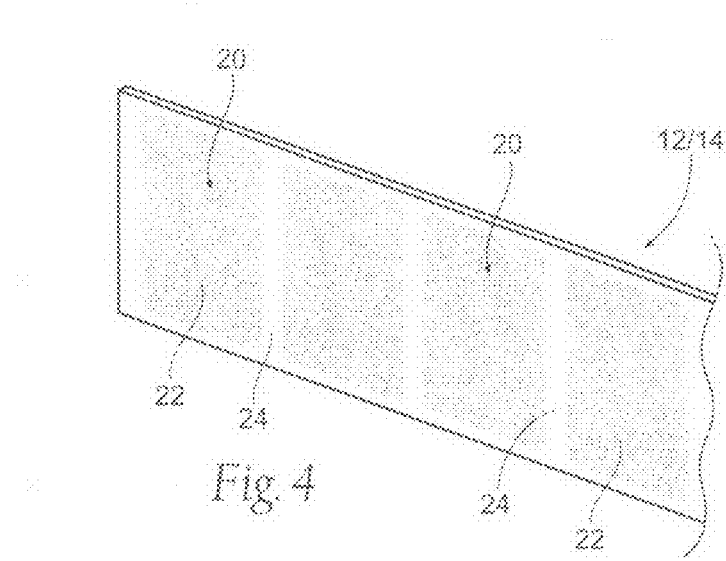
FIG. 4 is a perspective front view of an alternative embodiment of magnetic structure that can be used in the magnetic force system shown in FIG. 2, the structure including an array of polymer-bonded magnets.

The magnetic structures 12 and/or 14 can include one or more polymer-bonded magnets 20, as shown in FIG. 4. The polymer-bonded magnet 20 comprises magnetic particles 22 bound within a biocompatible polymer 24. The magnetic particles 22 can comprise either isotropic or anisotropic materials, e.g., NdFeB, SmCo, ferrite and/or alnico particles. The biocompatible polymer 24 can comprise, e.g., polycarbonate, silicone rubber, polyurethane, silicon elastomer, or a flexible or semi-rigid plastic. Fabric and/or textile and/or ceramic material can also be incorporated within the polymer matrix.

To form the polymer-bonded magnet 20, the magnetic particles 22 are compounded with the biocompatible polymer 24 in a desired proportion. The proportion of polymer 24 and magnetic particles 22 in the magnet 20 can be tailored to provide a desired degree of flexibility, elasticity, and magnetic strength.

The biocompatible polymer 24 is mixed with magnetic particles 22 in a predetermined ratio, and the mixture is compounded (i.e., kneaded). After compounding, the mixture can be molded into a desired shape. The molding methods can include, e.g., injection molding, compression molding, extrusion, and calendering.

Following molding, the molded component can be cut or machined as needed. Secondary surface coating using other biocompatible polymers may be applied, if desired. Alternatively, or in combination, two-stage molding may be accomplished, during which the molded component is over-molded with a layer of biocompatible polymer.

The finished component is then magnetized to possess the desired polarity. The polymer-bonded magnet 20 is thereby formed as a single piece, which reduces flux leakage.

In the system 10 shown in FIG. 2, the structures 12 and/or 14 could each include a polymer-bonded magnet 20. When positioned in the system 10 shown in FIG. 2, the polymer-bonded magnets 20 implanted in the pharyngeal wall and the tongue would possess like polarity, thereby creating the desired repelling force between them.

Finite element analysis shows that two repelling polymer-bonded magnets 20, each formed as a strip measuring 4 mm×10 mm×40 mm, are capable of creating a maximum energy product of about 0.8 MGOe. Finite element analysis based upon this energy product shows that the two polymer-bonded magnets 20 can generate a repelling force of more than 22 grams/cm$^2$ when they are positioned 12 mm apart. The magnetic properties of the strips and their dimensions can, of course, be changed to fit the applications.

The shape of a given polymer-bonded magnet 20 can be selected to best confirm to the anatomic site of implantation. It is believed that the biocompatibility, softness, and flexibility of a polymer-bonded magnet 20 make it tolerable during chronic implantation in tissue. Larger sizes of a given magnetic structure could also be considered, compared to use of conventional permanent magnets, because the similar mechanical properties of the polymer-bonded magnet 20 and the surrounding tissue.

The polymer-bonded magnet 20 can include through holes, and/or non-through holes, and/or complex surface configurations, and/or other surface textures, or combinations thereof, to promote tissue in-growth and implant stability. Further discussion of tissue ingrowth surfaces and materials follows.

3. Hybrid Magnetic Structures

Figure 5:
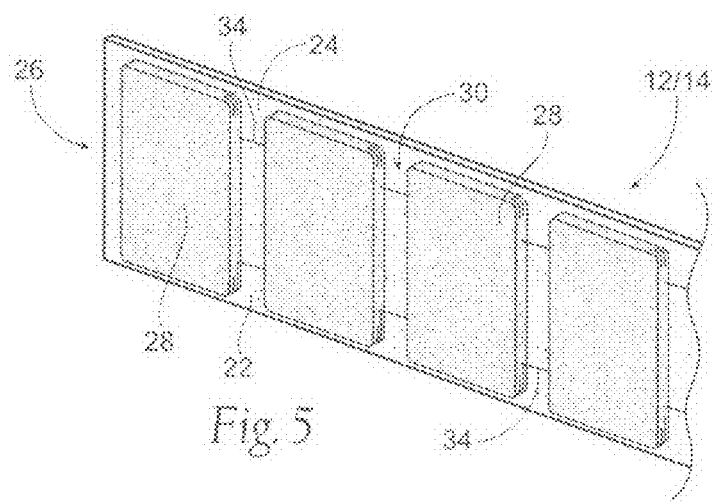
FIG. 5 is a perspective front view of an alternative embodiment of magnetic structure that can be used in the magnetic force system shown in FIG. 2, the structure including an array of permanent magnets mounted in a polymer-bonded magnetic array.

The magnetic structures 12 and/or 14 may include a hybrid magnetic structure 26, as shown in FIG. 5. The hybrid magnetic structure 26 shown in FIG. 5 comprises one or more discrete permanent magnets 28 encapsulated within a polymer-bonded magnetic matrix 30. As described above, the matrix 30 comprises magnetic particles 22 bound within a biocompatible polymer 24.

The permanent magnets 28 can comprise sintered, high energy, permanent magnets such as N45 or N48, i.e., possessing a maximum energy product of about 45-48 MGOe. If desired (as shown in FIG. 5), one or more threads 34 could connect the magnets 28 within the matrix 30, to improve stability of the structure 32.

As previously described, the magnetic particles 22 can comprise either isotropic or anisotropic materials, e.g., NdFeB, SmCo, ferrite and/or alnico particles. The biocompatible polymer 24 can comprise, e.g., polycarbonate, silicone rubber, polyurethane, silicon elastomer, or a flexible or semi-rigid plastic. Fabric and/or textile and/or ceramic material can also be incorporated within the polymer matrix. Within the structure 26, the permanent magnets 28 and the magnetic particles 22 are magnetized in the same flux direction.

The hybrid structure 26 takes advantage of the high magnetic strength of the sintered permanent magnets 28, and combines this benefit with the flexibility and biocompatibility of a polymer-bonded magnetic matrix 30. Furthermore, the presence of the permanent magnetic particles 22 between the high energy permanent magnets 28 pushes the flux lines emanating from the permanent magnets 28 farther away from the surface of the structure 26, as compared to permanent magnets 28 in a pure (non-magnetic) polymer matrix. This change in the flux lines reduces flux leakage.

Figure 6:
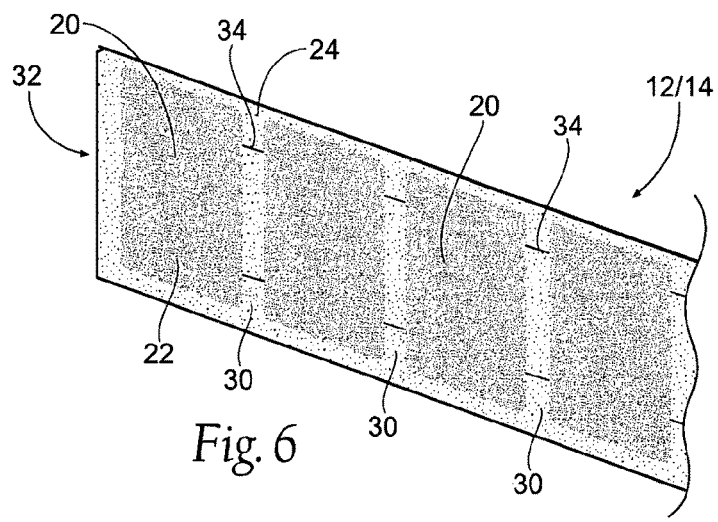
FIG. 6 is a perspective front view of an alternative embodiment of magnetic structure that can be used in the magnetic force system shown in FIG. 2, the structure including an array of polymer-bonded magnets incorporated into in a polymer-bonded magnetic array.

FIG. 6 shows an alternative embodiment of a hybrid magnetic structure 32. The structure 32 comprises one or more polymer-bonded magnets 20 (as shown in FIG. 4) encapsulated within a polymer-bonded magnetic matrix 30, as just described. The matrix 30 and the polymer-bonded magnets 20 each comprises magnetic particles 22 bound within a biocompatible polymer 24.

The density of magnetic particles 22 in the magnets 20 is desirably greater than the density of magnetic particles 22 in the matrix 30. This imparts more flexibility to the low-density matrix 30 and higher magnetic force to the higher density magnets 20. If desired (as shown in FIG. 6), one or more threads 34 could connect the higher density polymer-bonded magnets 20 within the matrix 30 to improve stability of the structure 32.

As previously described, the magnetic particles 22 can comprise either isotropic or anisotropic materials, e.g., NdFeB, SmCo, ferrite and/or alnico particles; and the biocompatible polymer 24 can comprise, e.g., polycarbonate, silicone rubber, polyurethane, silicon elastomer, or a flexible or semi-rigid plastic. Fabric and/or textile and/or ceramic material can also be incorporated within the polymer matrix. Within the structure 32, the magnetic particles 22 in the magnets 20 and in the matrix 30 are magnetized in the same flux direction.

The hybrid structure 32 takes advantage of the high density, high performance polymer-bonded magnets 20, and combines this benefit with the flexibility of the low-density polymer-bonded magnetic matrix 30. Furthermore, as described in connection with the hybrid structure 32 in FIG. 5, the presence of the permanent magnetic particles 22 between the high performance polymer-bonded magnets 20 pushes the flux lines emanating from the polymer-bonded magnets 20 farther away from the surface of the structure 32, as compared to polymer-bonded magnets 20 in a pure (non-magnetic) polymer matrix. This change in the flux lines reduces flux leakage.

In the system 10 shown in FIG. 2, the structures 12 and/or 14 could each comprise one of the hybrid magnetic structure 26 and/or 32. The structures 26 and/or 32 implanted in the pharyngeal wall and the tongue would possess like polarity, thereby creating the desired repelling force between them.

The shape of a given hybrid magnetic structure 26 or 32 can be selected to best confirm to the anatomic site of implantation. Furthermore, either hybrid magnetic structure 26 or 32 can include through holes 36 (see FIG. 7), and/or non-through holes, and/or complex surface configurations 38 (see FIG. 8), and/or other surface textures, or combinations thereof, to promote tissue in-growth and implant stability.

4. Layered Magnetic Structures

Figure 9:
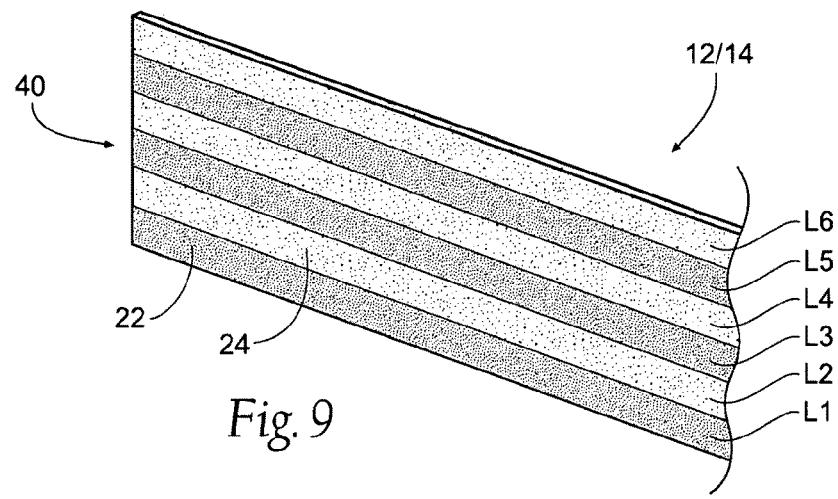
FIG. 9 is a perspective front view of an alternative embodiment of magnetic structure that can be used in the magnetic force system shown in FIG. 2, the structure including layers of polymer-bonded magnets incorporated into in a polymer-bonded magnetic array.

The magnetic structures 12 and/or 14 could include a layered magnetic structure 40, as shown in FIG. 9. The layered structure 40 comprises two or more layers of magnet particles 22 encapsulated in different densities within a biocompatible polymer 24. In FIG. 9, six layers L1 to L6 are shown for purposes of illustration, and it should be appreciated the number of layers can be greater than or less than six.

The density of magnetic particles 22 in layers L1, L3, and L5 is greater than the density of magnetic particles 22 in the neighboring layers L2, L4, and L6. The presence of the less dense layers L2, L4, and L6 imparts overall flexibility to structure 40, whereas the presence of the more dense layers L1, L3, and L5 imparts higher magnetic force. The juxtaposition of the less dense layers L2, L4, and L6 between the more dense layers L1, L3, and L5 pushes the flux lines emanating from the higher density layers L1, L3, and L5 farther away from the surface of the structure 40, as compared to uniform density polymer-bonded magnetic layers. This change in the flux lines reduces flux leakage.

As previously described, the magnetic particles 22 can comprise either isotropic or anisotropic materials, e.g., NdFeB, SmCo, ferrite and/or alnico particles; and the biocompatible polymer 24 can comprise, e.g., polycarbonate, silicone rubber, polyurethane, silicon elastomer, or a flexible or semi-rigid plastic. Fabric and/or textile and/or ceramic material can also be incorporated within the polymer matrix. Within the structure 40, the magnetic particles 22 in the layers L1 to L6 are magnetized in the same flux direction.

Figure 10:
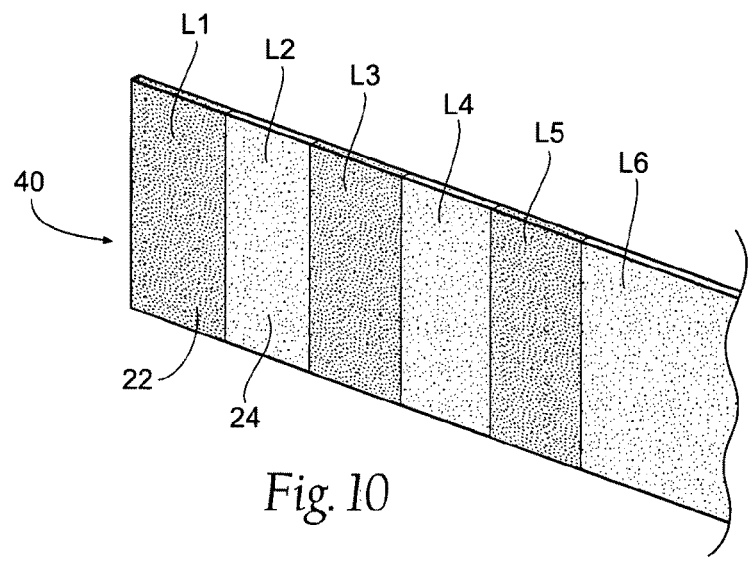
FIG. 10 is a perspective front view of an alternative embodiment of magnetic structure that can be used in the magnetic force system shown in FIG. 2, the structure including layers of polymer-bonded magnets incorporated into in a polymer-bonded magnetic array proving a graduated flux field.

In FIG. 9, the density of magnetic particles 22 in the higher density layers L1, L3, and L5 is shown to be generally the same. In an alternative arrangement (see FIG. 10), the density of magnetic particles 22 in the higher density layers L1, L3, and L5 can gradually increase. This provides a change in the flux density across the surface of the structure 40.

In the system 10 shown in FIG. 2, the structures 12 and/or 14 could each comprise a layered magnetic structure 40, or a layered magnetic structure 40 used in combination with another type of magnetic structure, such as a flexible array of discrete permanent magnets, polymer-bonded magnets, or hybrid magnetic structures 26 and/or 32. Regardless, the structures 12 and 14 implanted in the pharyngeal wall and the tongue would possess like polarity, thereby creating the desired repelling force between them.

Figure 11:
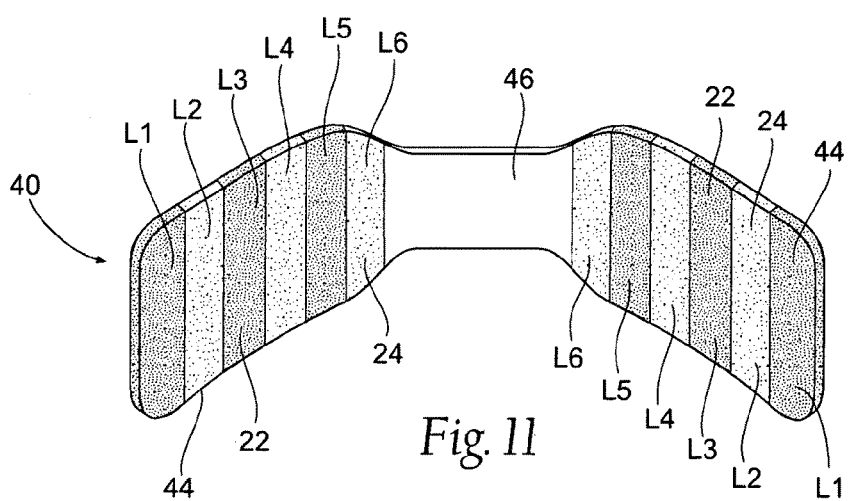
FIG. 11 is a perspective front view of a magnetic structure of the type shown in FIG. 9 or 10, having magnetic end regions separated by a non-magnetic center, the end regions comprising layers of polymer-bonded magnets incorporated into in a polymer-bonded magnetic array.

The shape of a layered magnetic structure 40 can be selected to best confirm to the anatomic site of implantation. For example, as shown in FIG. 11, the layered structure 40 can comprise end portions 44 separated by a connecting strip 46. Each end portion 44 includes the layers L1 to L6 of magnetic particles 22 encapsulated in different densities within a biocompatible polymer 24, as previously described. Alternatively, the layers L1 to L6 could provide a variation of densities, or the density of magnetic particle 22 within one or both end portions 44 coukld be uniform. The connecting strip 46 comprises the biocompatible polymer 24 free of magnetic particles 22. The magnetic particles 22 in the end portions 44 are magnetized to have the same polarity, so that the end portions repel each other. The intermediate strip 44, being free of magnetic particles 22, does not interfere with the repelling force.

Figure 7:
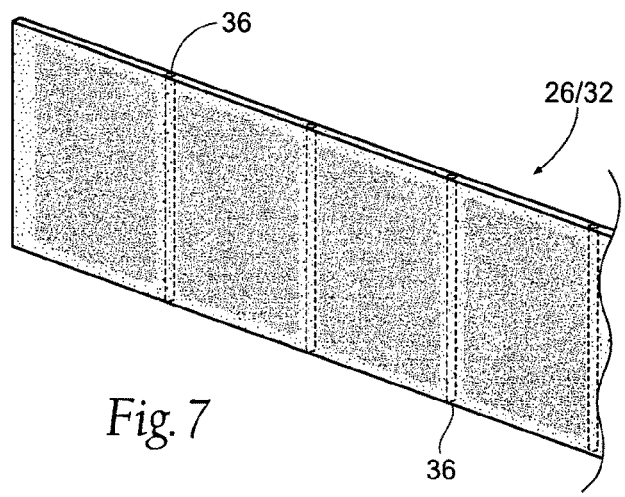
FIGS. 7 and 8 are perspective front views of the magnetic structure shown in FIG. 6, showing the inclusion of structures or geometries that encourage tissue ingrowth to secure the structure within tissue.
Figure 8:
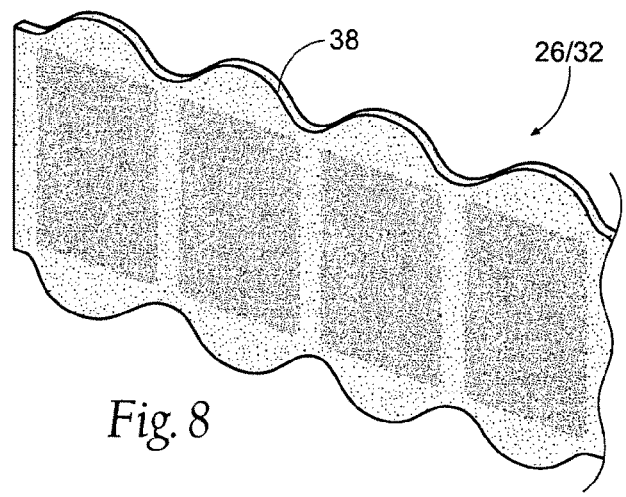
Figure 12:
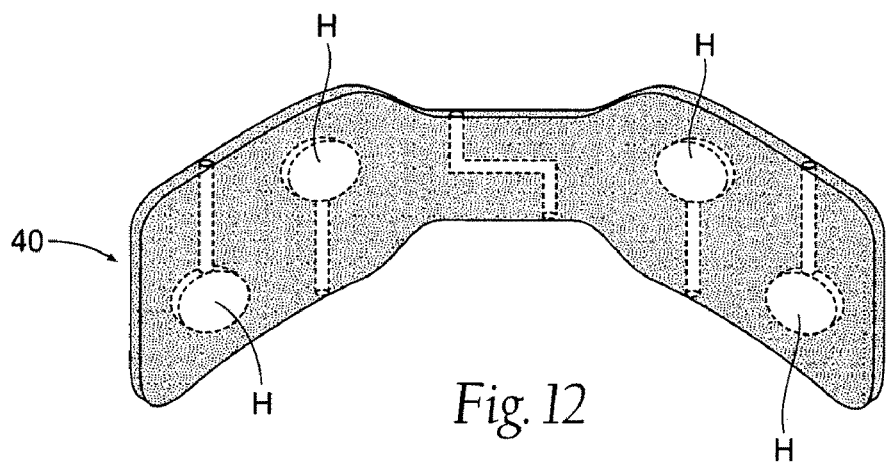
FIG. 12 is perspective front view of the magnetic structure shown in FIG. 11, showing the inclusion of structures that encourage tissue ingrowth to secure the structure within tissue.

As FIG. 12 shows, the structure 40 can include surface texturing (shown as a pattern of non-through holes H), to promote tissue in-growth and implant stability. Through holes (as shown in FIG. 7), and/or complex surface configurations (as shown in FIG. 8), and/or other surface textures, or combinations thereof, can be used for the same purpose.

C. Focusing the Magnetic Flux of Magnetic Structures

Regardless of the type of magnetic structure that is implanted, it is desirable to achieve high repelling forces using an array of magnets of relatively small size, which can be tolerated by the body without discomfort. A way to achieve this objective is to include means for focusing the magnetic flux in a desired direction, while also reducing the flux in other directions. The focusing of magnetic flux can make possible the use of smaller magnets. The focusing of magnetic flux can also impart stability to the implanted structure, to resist migration within tissue.

Figure 13:
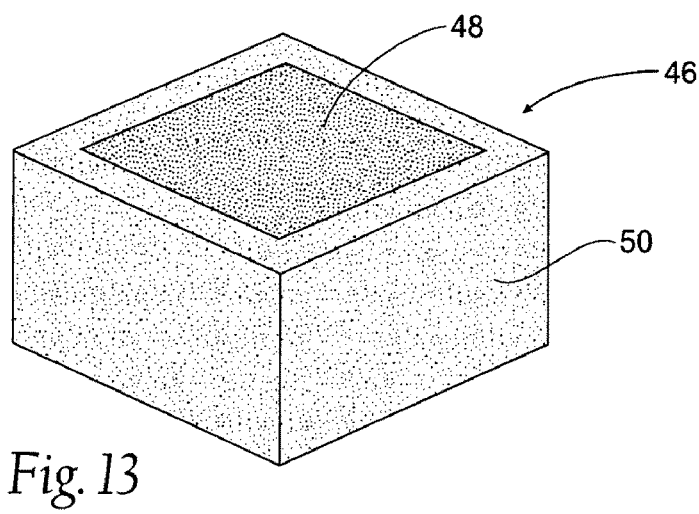
FIG. 13 is a perspective side views of a shielded magnetic structure comprising a permanent magnet core enclosed within a soft ferromagnetic material, which exposes but a single pole surface to focus the flux filed in that direction.

FIG. 13 shows a magnetic structure 46 comprising a magnetic core 48 and an overlaying flux shield 50 that includes a soft ferromagnetic material. The magnetic core 48 can comprise a rare earth permanent magnet, or a polymer-bonded magnet, or a hybrid magnetic structure, or a layered magnetic structure, all having previously been described. The soft ferromagnetic material of the flux shield 50 has very high permeability and saturation magnetization, but very low intrinsic coercivity. Examples of known soft ferromagnetic materials include Iron (Fe); Nickel (Ni); Permendur; MuMetal, low-carbon steels, Iron-Cobalt alloys (Fe—Co); silicon steels; and amorphous alloys.

As the following examples demonstrate, the presence of a flux shield 50 of a soft ferromagnetic material focuses and enhances the magnetic field of the core 48 in directions that the shield 50 does not overlay. In FIG. 13, the flux shield 50 overlays all but one pole of the core 48. However, as will be shown later, the flux shield 50 need overlay only one pole surface of the core 48 to achieve a flux focusing effect.

EXAMPLE 1

Unshielded Core

Figure 14A:
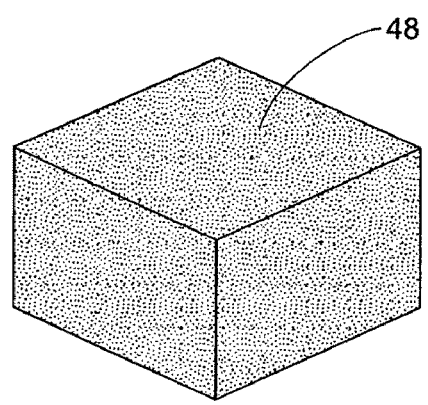
FIGS. 14A, 14B, and 14C show an unshielded permanent magnet core (FIG. 14A), its unfocused flux density distribution (FIG. 14B), and the likewise unfocused bell shaped distribution of the Z component of its flux density.
Figure 14B:
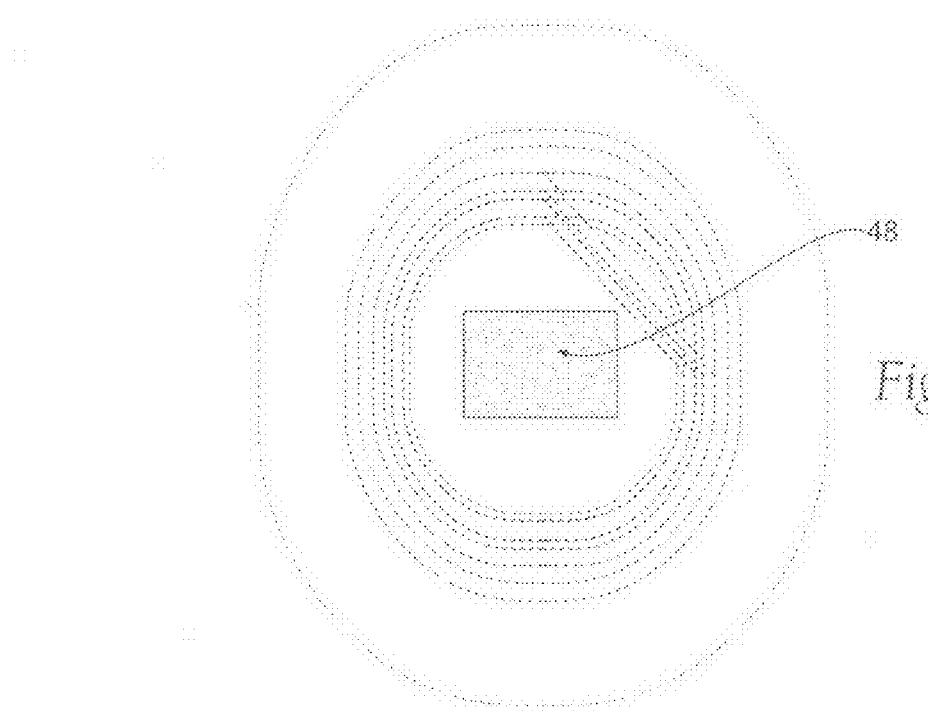
Figure 14C:
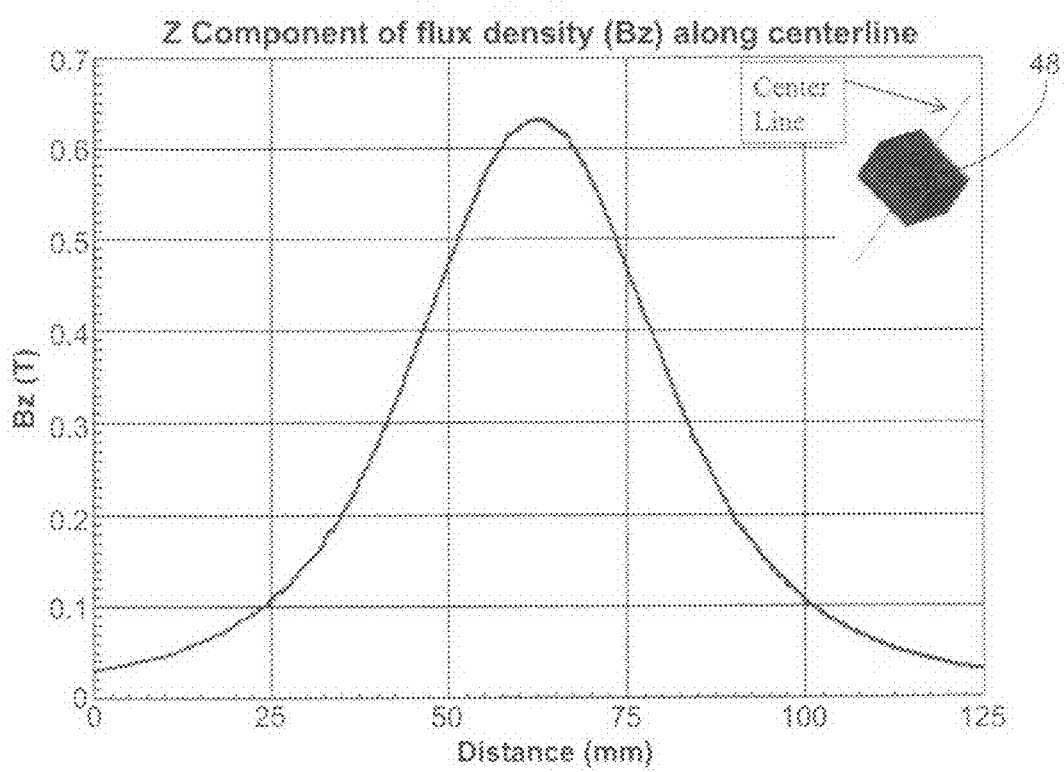

FIG. 14A shows a core 48 comprising a permanent magnet measuring 40 mm×40 mm×25 mm (i.e., a volume of 40,000 mm$^3$). FIG. 14B shows the total flux density distribution on the YZ plane, based upon finite element modeling, of the magnetic field generated by the permanent magnet. FIG. 14B shows the magnetic field emanating in all directions in the YZ plane about the magnet. FIG. 14C shows the magnitude of the Z component of flux density (Bz) taken at increasing distances from the top magnet surface along its center line. FIG. 14C generally shows a bell shaped curve, with a maximum Bz(T) of 0.6 at a distance of about 62 mm from the magnet surface, with gradual increases with decreasing distances and gradual decreases with increasing distances.

EXAMPLE 2

Shielded Core

Figure 15A:
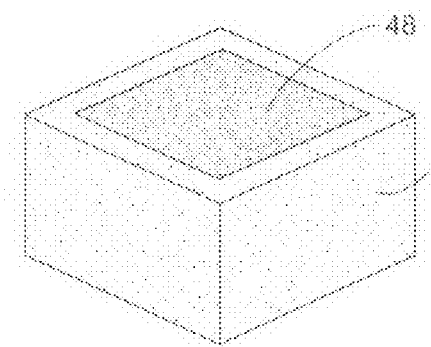
FIGS. 15A, 15B, and 15C show a shielded permanent magnet core of the type shown in FIG. 13 (in FIG. 15A), its focused flux density distribution (FIG. 15B), and the likewise focused spike-shaped distribution of the Z component of its flux density.

FIG. 15A shows a core 48 comprising a permanent magnet smaller than the magnet of Example 1, measuring 30 mm×30 mm×20 mm (i.e., having a lesser volume of 18,000 mm$^3$). The magnet has been placed within a flux shield 50. The flux shield comprises a box made from a soft ferromagnetic material. The box covers all but one pole surface of the permanent magnet.

Figure 15B:
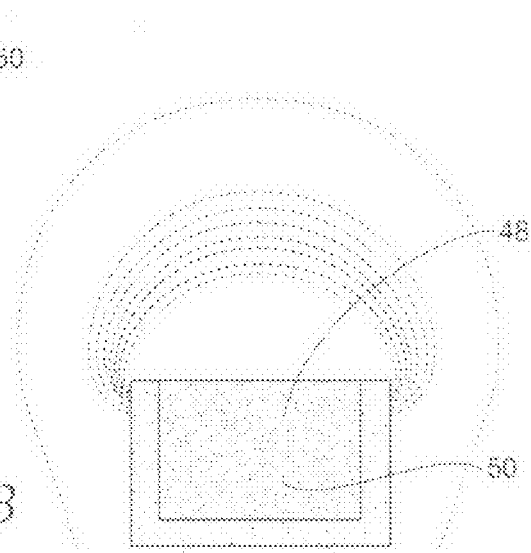
Figure 15C:
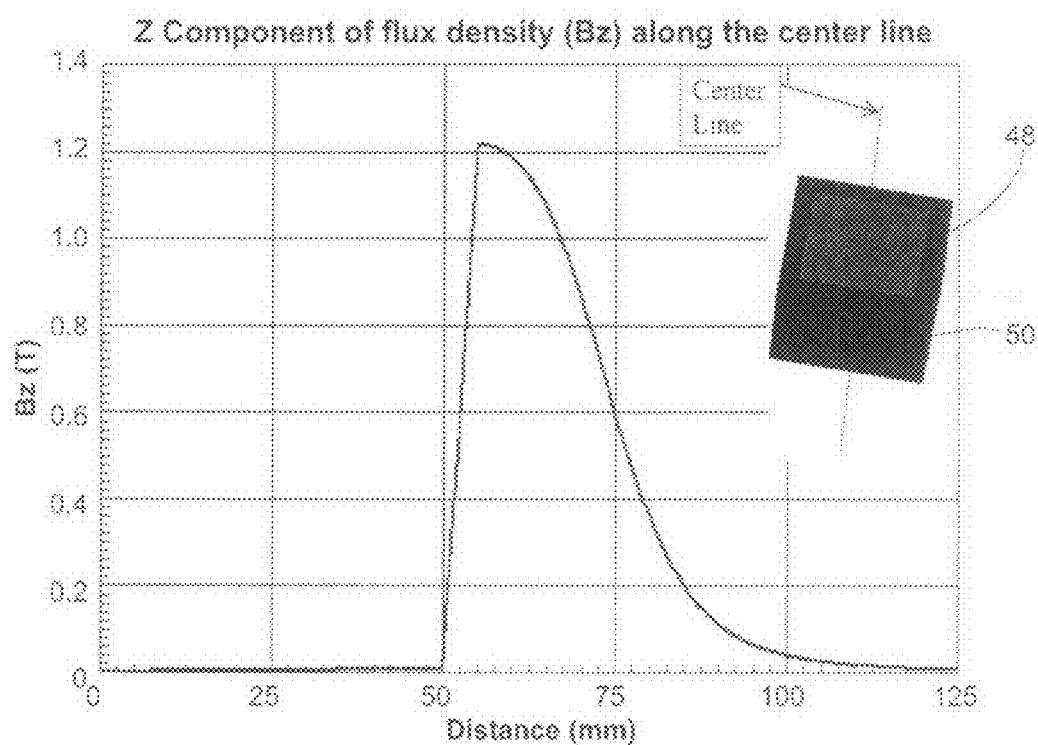

FIG. 15B shows the total flux density distribution on the YZ plane, based upon finite element modeling, of the magnetic field generated by the permanent magnet when housed within the box. FIG. 15B shows that the presence of the ferromagnetic material of the box significantky alters the distribution pattern of the flux density of the field on the YZ plane. The magnetic field is demonstrably focused in the direction of the field that is not shielded by the ferromagnetic material. FIG. 15C shows the magnitude of the Z component of flux density (Bz) taken at increasing distances from the unshielded pole surface along its center line. FIG. 15C confirms the focused nature of the magnetic field. FIG. 15C also shows an increase in the flux density of the Z component in Example 2, despite the use of a magnet of significantly lesser volume than in Example 1. Unlike the curve in FIG. 14C, the curve in FIG. 15C is not bell shaped. The Z component of the flux density BZ suddenly spikes at a maximum Bz(T) of 1.2 at a distance of about 55 mm from the unshielded pole, and thereafter maintains a magnitude above 0.6 Bz(T)—i.e., above the maximum flux density of the Z component of Example 1—at increasing distances up to about 75 mm from the single unshielded pole of the magnet.

A comparison of FIGS. 14B/C with FIGS. 15B/C demonstrates the ability of a soft ferromagnetic material to shield and to focus the magnetic field emanating from a permanent magnet.

EXAMPLE 3

Alternative Shielded Magnets

Figure 16A:
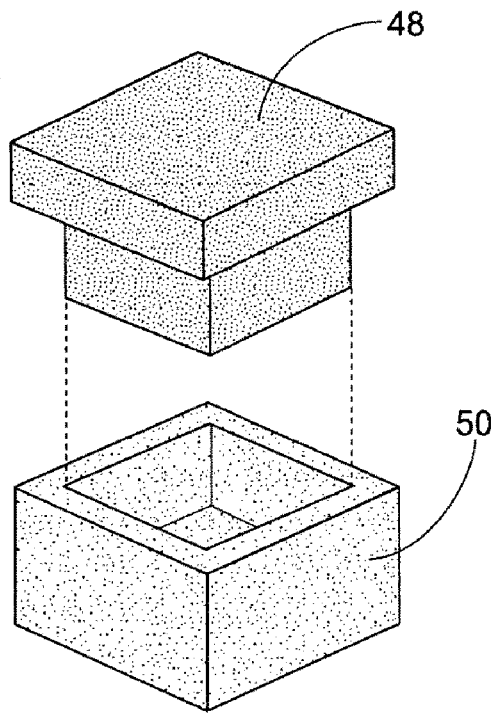
FIGS. 16A and 16B are perspective side views of alternative embodiments of shielded magnetic structures each having a focused flux density distribution and a likewise focused spike-shaped distribution of the Z component of its flux density performance characteristics comparable to that shown in FIGS. 15B and 15C.
Figure 16B:
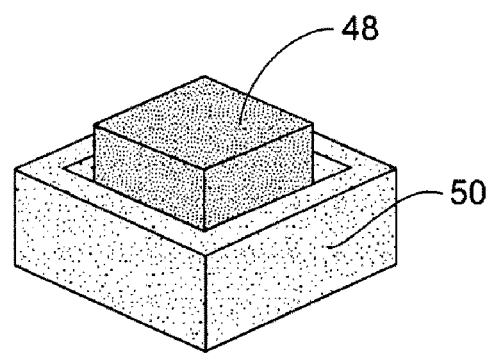

FIGS. 16A and 16B show alternative embodiments of magnetic cores 48 comprising permanent magnets with flux shields 50 of soft ferromagnetic materials. Finite element analysis of these alternative embodiments show the focused flux density distribution shown in FIG. 15B, as well as the spike-curve configuration, shown in FIG. 15C, of the Z component of flux density (Bz) taken at increasing distances from the unshielded magnet pole along its center line.

EXAMPLE 4

Single Pole Shield

Figure 17A:
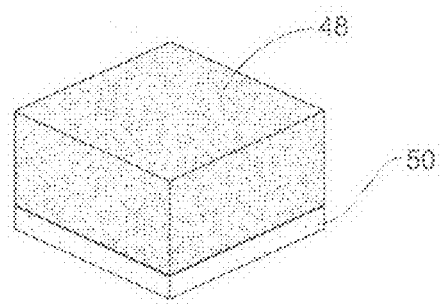
FIGS. 17A and 17B show an alternative embodiment of a shielded magnetic structure comprising a permanent magnet core shielded on one pole surface by a soft ferromagnetic material (FIG. 17A) and the focused spike-shaped variation of the Z component of its flux density (FIG. 17B).
Figure 17B:
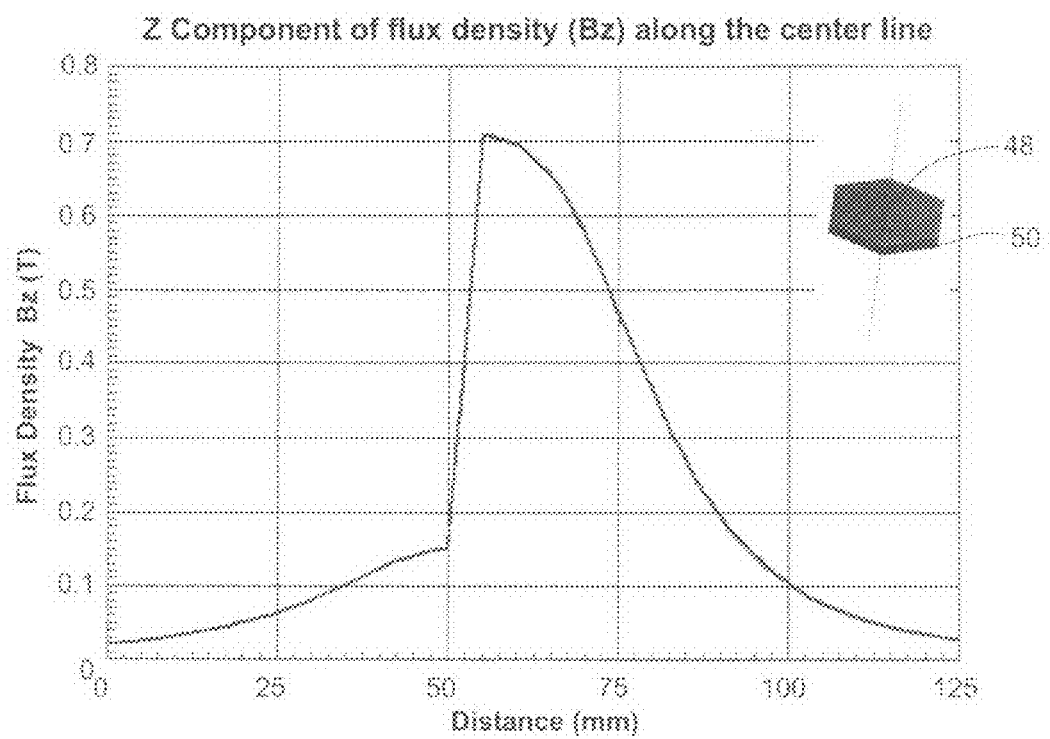

FIG. 17A shows magnetic core 48 comprising a permanent magnet having generally the same measurements as the magnet in Example 1. In this embodiment, the flux shield 50 overlays only one pole of the magnet. FIG. 17B shows that the magnitude of the Z component of flux density (Bz) taken at increasing distances from the unshielded magnet pole along its center line has been ltered by the presence of the single pole flux shield 50. FIG. 17B shows the same spike-curve configuration shown FIG. 15C, demonstrating that the presence of the single pole flux shield 50 has focused the magnetic field in the direction of the unshielded magnet pole. FIG. 17B also demonstrates that the maximum strength of the magnetic field has likewise been increased, from 0.6 Bz(T) in Example 1 to 0.7 Bz(T) in Example 4. FIG. 17B demonstrates the ability of single pole flux shield 50 of soft ferromagnetic material to shield and focus the magnetic field emanating from a permanent magnet.

D. Reducing Instability of the Magnetic Structures

Regardless of the type of magnetic structure that is implanted, it is also desirable to minimize the effects of instability due to magnetic field forces. It is also desirable to minimize migration or twisting should misalignment between the magnetic field forces of opposed magnetic structures 12 and 14 occur. If repelling like poles become misaligned, unlike poles may seek to attract and align.

Figure 18A:
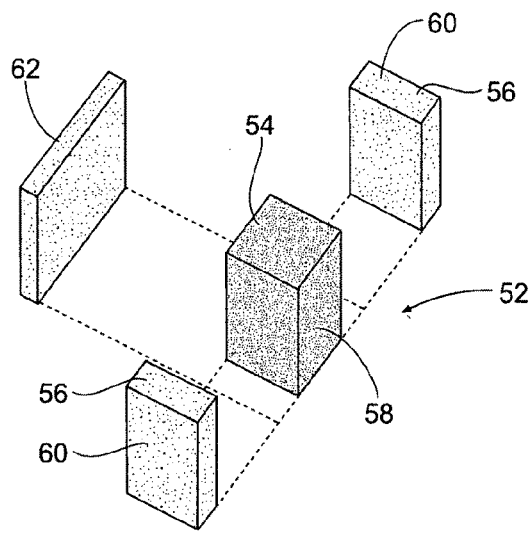
FIGS. 18A and 18B are perspective side views, respectively exploded and assembled, of a stabilized magnetic assembly comprising a permanent magnet core, an attached pair stabilizing permanent magnets, and a single pole shield of soft ferromagnetic material of a type shown in FIG. 17A.
Figure 18B:
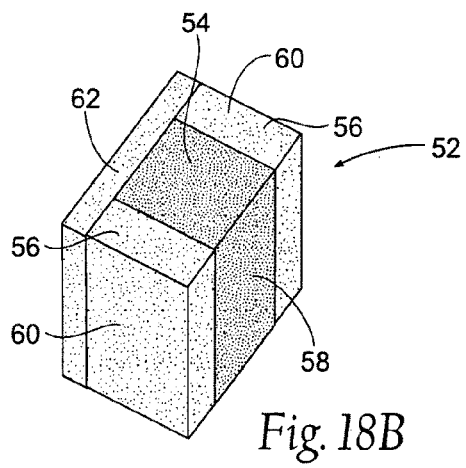

A way to minimize the effects of instability is to include stabilization magnets having repelling poles normal or at an acute angle to the major repelling pole. By way of illustration, FIGS. 18A and 18B show a stabilized magnetic structure 52 comprising a magnetic core 54 joined to a pair of stabilizing magnets 56.

The magnetic core 54 can comprise a rare earth permanent magnet, or a polymer-bonded magnet, or a hybrid magnetic structure, or a layered magnetic structure, all having previously been described. The magnetic core 54 has a repelling pole 58 that is sized and configured to be primarily responsible for the repelling force needed for a given structure.

Each stabilizing magnet 56 is secured to a side of the repelling magnetic core 54, e.g., by adhesive, welding, molding, crimping, or soldering. The stabilizing magnets 56 comprise rare earth permanent magnets, or a polymer-bonded magnet, or a hybrid magnetic structure, or a layered magnetic structure, all having previously been described. The stabilizing magnets 56 each has a repelling pole 60 (i.e., having the same polarity as the repelling pole 58). The surfaces of the repelling poles 60 of the stabilizing magnets 56 are oriented at right angles to the repelling pole 58 of the magnetic core 52. The poles 60 of the permanent stabilizing magnets 56, like the repelling pole 58 of the magnetic core 52, are all like the poles of the magnet(s) on the opposing magnetic structure.

Should rotational misalignment of one magnetic structure occur, the outward facing poles 60 of the permanent stabilizing magnets 56 will, to a greater or lesser degree, continue to face the like poles of the magnet(s) on the other magnetic structure. Since the outward facing poles 60 of the permanent stabilizing magnets 56 are like the poles of the other structure, the repelling nature of magnetic field between the two structures remains the same—the two magnet structures 12 and 14 continue to repel each other. Rotational misalignment may lead to a diminution of the magnetic force field, but the magnetic force field is itself still a repelling field. Destabilizing magnetic fields are reduced due to misalignment, to reduce twisting or otherwise destabilizing either structure 12/14.

As further shown in FIGS. 18A and 18B, the stabilized magnetic structure 52 may includes a shielding pole piece 62 made of a soft ferromagnetic material secured to the opposite pole face of the magnetic core 54. The shielding pole piece 62 serves to alter the distribution and the magnitude of the Z component of flux density (Bz), in the manner previously demonstrated, providing the spike-shaped performance characteristic shown in FIG. 17B. The shielding pole piece 62 focuses the magnetic flux in the desired direction.

Figure 18C:
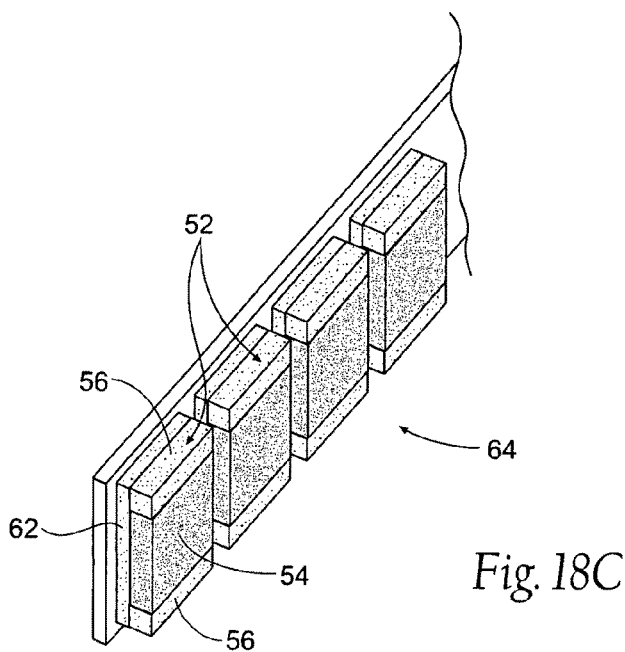
FIG. 18C is a perspective front view of an alternative embodiment of stabilized magnetic structure that can be used in the magnetic force system shown in FIG. 2, the structure including an array of stabilized magnetic assemblies shown in FIG. 18B mounted on a flexible carrier.

In a representative embodiment, the repelling magnetic core 54 has a dimension of 2 mm×2 mm×4 mm. Each stabilizing magnet 56 has a dimension of 1 mm×2 mm×4 mm. The shielding pole piece 62 has a dimension of 4 mm×4 mm×0.5 mm. The resulting structures 52 can be assembled into arrays 64 of stabilized magnetic structures 52 (see FIG. 18C). On each array 64, the stabilized magnet structures 52 are spaced apart by about 1 mm. Arranged in a facing, repelling relationship at a distance of about 12 mm, finite element analysis shows that a repelling force between the arrays 64 can be generated, which can be increased or decreased by changing the dimensions of the stabilized magnetic structures 52 or the arrays 64. The presence of the shielding pole piece 62 focuses and increases the flux density in the desired direction between arrays 64. The presence of the stabilizing magnets 56 provides positional stability, to which the shielding pole piece 62 also contributes by reducing flux density in undesired directions.

As FIG. 18E shows, should the array 64 include more than one row of adjacent magnetic structures 52 with stabilizing magnets 56, the surfaces of the magnetic structures 52 that face inward within the array 64 need not carry stabilizing magnets 56. In this arrangement, the stabilizing magnets 56 are located along the outside edges of the multiple row array 64.

Positional stability of a given array of magnets can also be enhanced without use of stabilizing magnets 56. As shown in FIGS. 18D(1) and 18D(2), and as previously described, magnetic cores 54 (comprising e.g., rare earth permanent magnets, or polymer-bonded magnets, or hybrid magnetic structures, or layered magnetic structures) can be arranged along a flexible carrier C. Each magnetic core 54 has a repelling pole 58 that is sized and configured for the repelling force needed for a given structure. Enhanced positional stability in such an array can be achieved by reorienting a repelling pole 58 of one of the magnetic cores 54 by ninety-degrees, in either direction (shown, respectively, in FIGS. 18D(1) and 18D(2) relative to the orientation of its neighboring cores 54. Within a given array, one or more cores 54 can be reoriented in this manner in either a random or repeating pattern. Should rotational misalignment of one magnetic array relative to another magnetic array occur, the presence of at least one reoriented core within one or both of the arrays will, to a greater or lesser degree, maintain the repelling nature of magnetic field between the two structures. Destabilizing magnetic fields are reduced due to misalignment, to reduce twisting or otherwise destabilizing either array.

II. Fixation of Structures Implanted in Tissue

Implants of the types described herein, or of other designs and functions, can be fixed percutaneously into the pharyngeal wall and/or tongue (the locations shown in FIG. 2), and/or elsewhere in the pharyngeal conduit, and/or elsewhere in the body in various ways. It should be appreciated that, while the description of various fixation techniques that follows shows the implant to be a magnetic structure, and the implantation site being in the pharyngeal conduit, such description is for the purpose of illustrating the features and benefits of a given technique. The features and benefits that will be described are broadly applicable to any implant placed within an implantation site anywhere within the body.

A. Use of Mechanical Fixation Materials

The position of implanted magnetic structures 12/14 or any implant in general can be fixed against migration in a targeted tissue region, e.g., within the pharyngeal conduit, using conventional mechanical fixation materials and techniques known in the surgical arts, e.g., resorbable or non-resorbable sutures, screws, staples, darts, clips, adhesives, or glues such as cyanoacrylate, or cements such as polymethyl methacrylate (PMMA) cement. For example, the structures 12/14 or any implant in general can include preformed apertures to accommodate the fixation material, i.e., sutures, screws, staples, darts, or clips. Fixation to tissue enhances the fixation function of the implanted structure.

The tissue to which a given implant is fixed can include soft tissue, such as mucosa, submucosa, fascia, or muscle in the pharyngeal walls, the base of the tongue; the vallecula; the soft palate with uvula; the palatine tonsils with associated pillar tissue, and the epiglottis.

The tissue can also include bone within the pharyngeal conduit, e.g., a hyoid bone or a vertebra.

Various systems for mechanically securing implanted magnetic structures in tissue, muscle, or bone are shown in U.S. patent application Ser. No. 10/718,254, filed Nov. 20, 2003 and entitled "Devices, Systems, and Methods to Fixate Tissue Within the Regions of the Body, Such as the Pharyngeal Conduit," which is incorporated herein by reference.

A given magnetic structure or implant can implanted in either a horizontal or vertical anatomic orientation, and/or in a linear or curvilinear pattern within the pharyngeal conduit or elsewhere in the body.

B. Fixation in Muscle or Other Soft Tissue

1. Direct Approach (The Flap)

Implants can be placed directly within the mucosa, or the submucosa, or against the fascia, or against or within muscle within the pharyngeal wall and/or tongue (the locations shown in FIG. 2) or elsewhere in the body by raising a surgical flap.

Using a flap approach, no sutures need to be placed through the mucosa into the implant. It has been discovered that placement of sutures through the mucosa can provide a conduit effect along the suture line from the contaminated oral cavity into the sterile implant pocket. Also, when using a flap approach, the implant can be better stabilized under direct vision, so the implant can be better positioned, since visualization is direct.

The flap approach can be accomplished in a single stage or in two stages. Either approach can be used to place a magnetic structure or any other type or style of implant in the pharyngeal conduit or elsewhere in the body.

a. Single Stage Flap Approach

FIGS. 19A to 19D show the use of a single stage flap approach to place an implant in a lateral pharyngeal wall. FIGS. 20A to 20D show the use of single stage flap approach to place an implant in a posterior-lateral pharyngeal wall. FIGS. 21A to 21D show the use of a single stage flap approach to place an implant in a posterior region of a tongue.

Figure 19A:
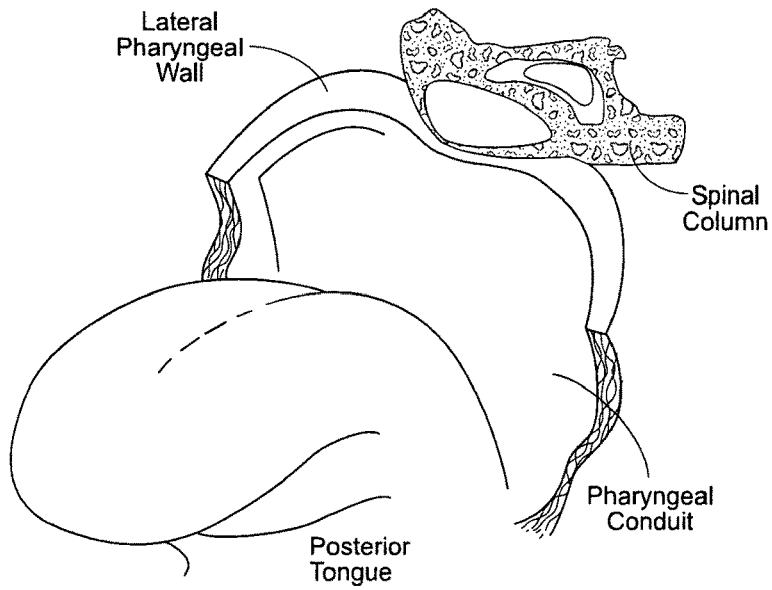
FIGS. 19A, 19B, 19C, and 19D are perspective anatomic views of a tongue and adjacent pharyngeal wall, simplified and diagrammatic, showing the formation of a surgical flap on a lateral pharyngeal wall and the implantation of an implant in the flap.
Figure 19B:
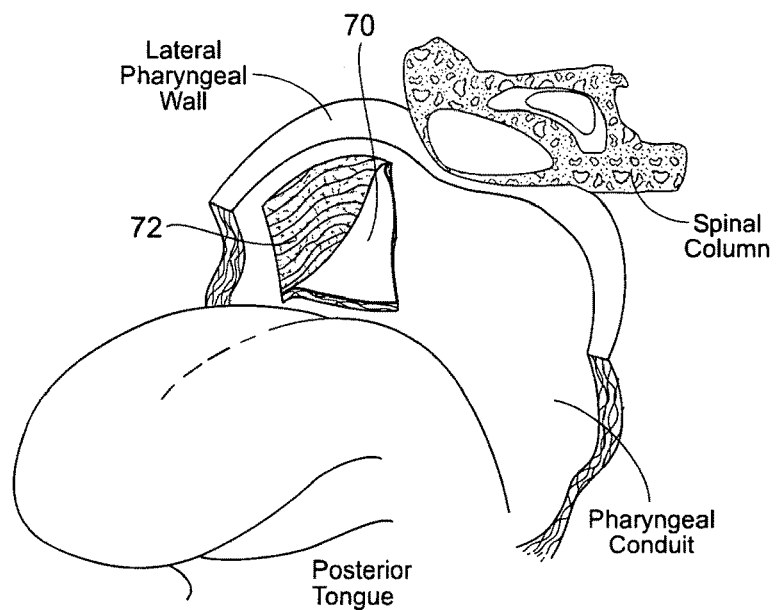
Figure 20A:
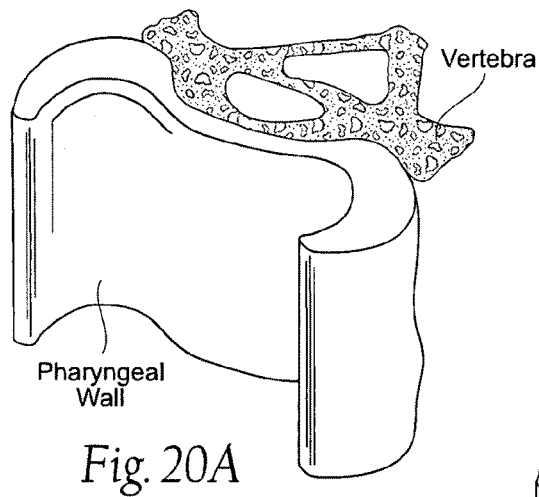
FIGS. 20A, 20B, 20C, and 20D are perspective anatomic views of a pharyngeal wall, simplified and diagrammatic, showing the formation of a surgical flap on a posterior-lateral pharyngeal wall and the implantation of an implant in the flap.
Figure 20B:
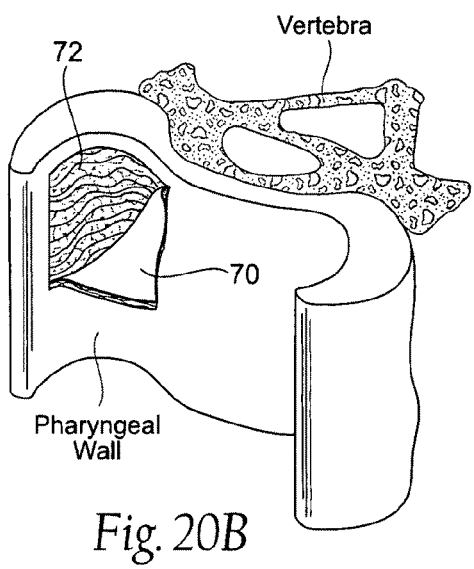
Figure 21A:
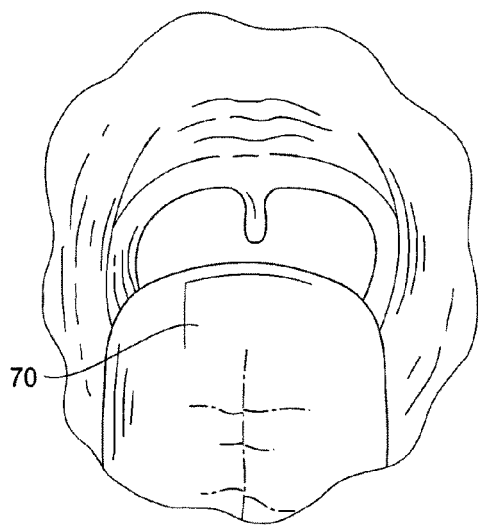
FIGS. 21A, 21B, 21C, and 21D are anatomic views of a tongue within an oral cavity, simplified and diagrammatic, showing the formation of a surgical flap on the posterior tongue and the implantation of an implant in the flap.
Figure 21B:
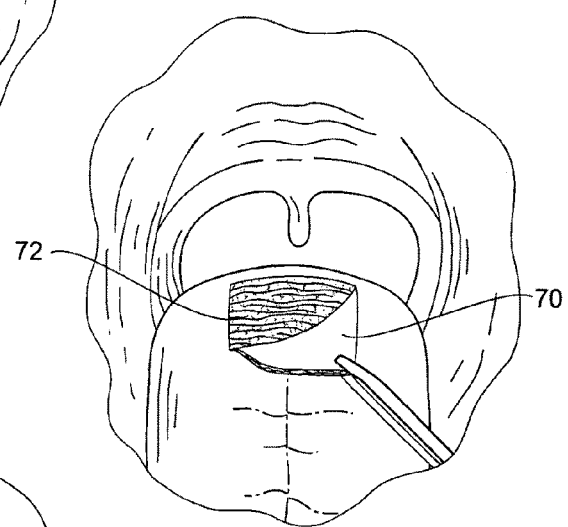

After transoral exposure of the oral cavity, lateral wall or tongue, a flap 70 is formed in the tissue plane (see FIGS. 19A, 20A, and 21A). The flap 70 is formed by using an appropriate surgical cutting instrument to form an incision having a desired shape. The formed flap 70 can be of various shapes and positions depending on the desired location, shape and proposed function of the implant. As examples, bilateral pharyngeal wall flaps 70 can be configured in a curvilinear upside down "L" shape for placement of directly opposite implants. A superior or inferior based "U" shaped flap can be configured along the posterior and posterior-lateral pharyngeal walls for placement of two posterior-lateral implants either connected or not across the midline. Tongue flaps of similar configurations can likewise be elevated.

Figure 19C:
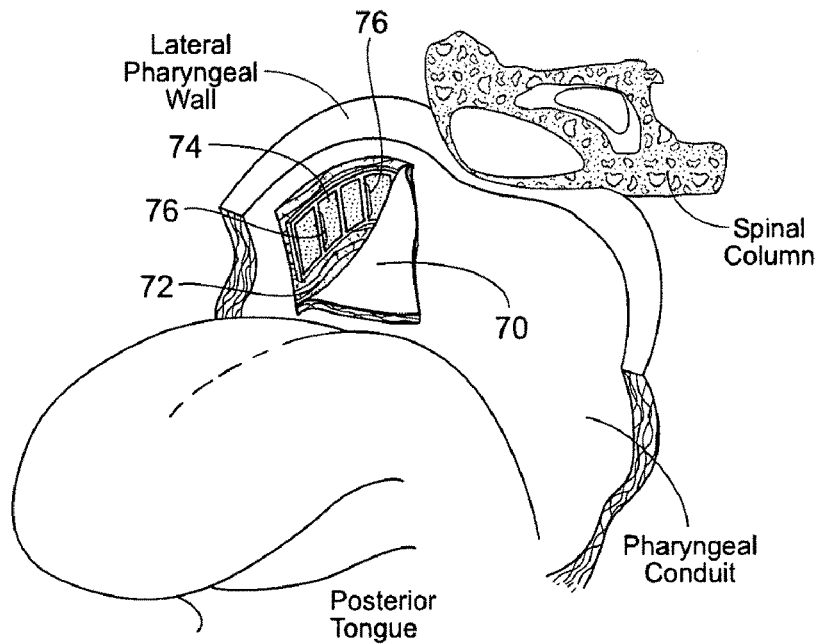
Figure 20C:
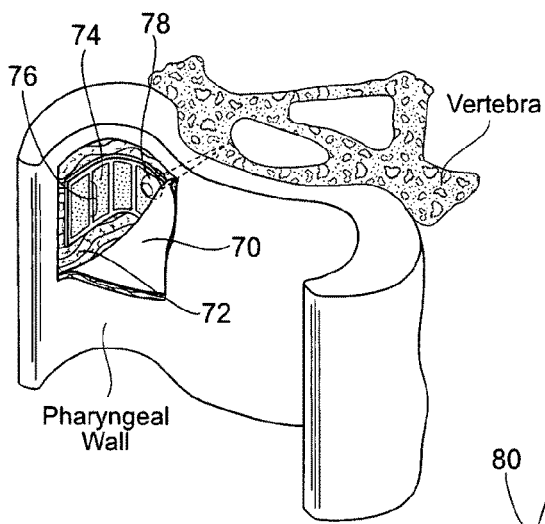
Figure 21C:
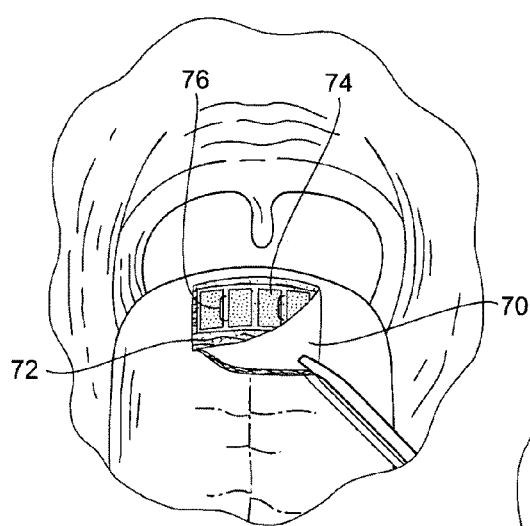

Elevating a flap 70 can expose underlying muscle 72 (see FIGS. 19B, 20B, and 21C), which can be fascial covered. Excellent exposure is afforded for controlled placement of the implants. The pharyngeal flaps (both lateral and posterior-lateral) can expose pharyngeal constrictor muscles, and the tongue flap can expose genioglossal muscle, As FIGS. 19C, 20C, and 21C shows, a selected implant 74 is then stabilized within the mucosa, or the submucosa, or against the fascia or against or within muscle 72 in each elevated flap 70, e.g., with simple sutures 76, and/or mattress sutures, and/or staples, and/or clips, and/or darts, and/or hooks or fasteners attached to or formed on the biocompatible body of the structure (which can be biodegradable, if desired). The implant 74 is desirably dipped or impregnated with an antibiotic. In the case of the posterior-lateral flap (see FIG. 20C), bone anchors 78 placed into the anterior vertebral column can be used.

It should be appreciated that, instead of forming a flap, a surgical pocket can be formed to receive the implant. The pocket is formed by dilating tissue by use of a trocar or expandable dissector, to open a tissue space to receive an implant. Using a pocket approach, like the flap approach, no sutures need to be placed through the mucosa into the implant. The implantation and implant fixation techniques described herein with regard a surgical flap apply to surgical pockets as well.

Figure 19D:
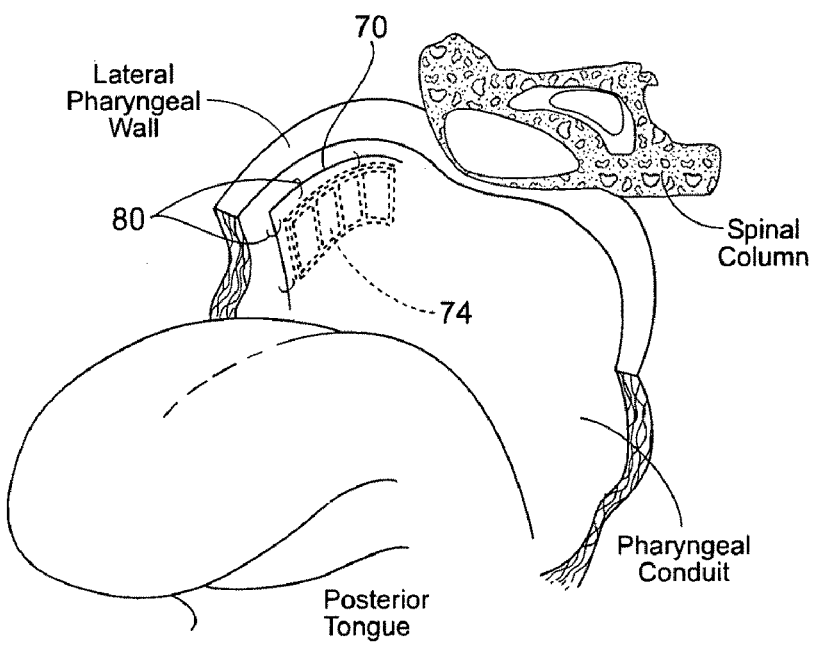
Figure 20D:
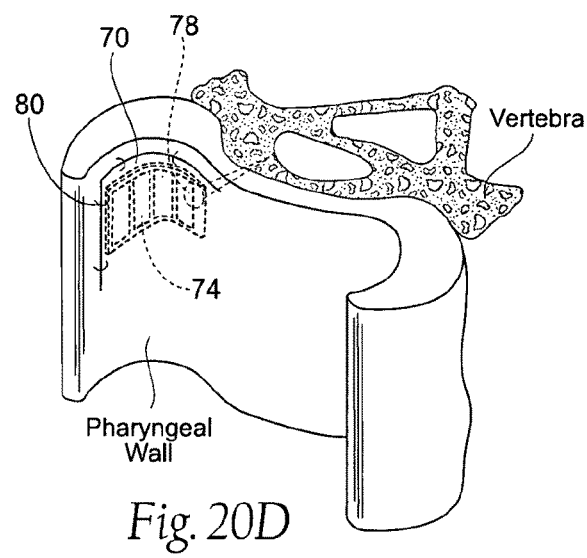
Figure 21D:
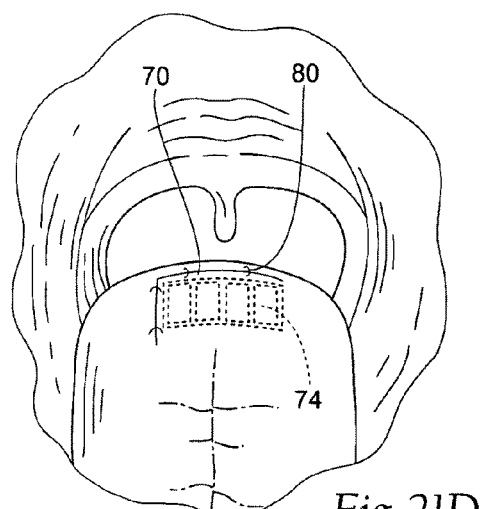

As FIGS. 19D, 20D, and 21D show, with the implant 74 now stabilized a distance away from the flap incision, the flaps 70 (or pocket) can be closed, e.g., with one or more absorbable or non-absorbable sutures 80, adhesives, or glues such as cyanoacrylate, or cements such as polymethyl methacrylate (PMMA) cement. An absorbable sutures 80 can be rapidly dissolving (e.g., seven days), or comprise a longer lasting absorbably suture such as Vicryl™ material, Supplemental systemic antibiotics are desirably utilized, which can be delivered into the flap 70 (or pocket) before or after implant placement.

Agents to stimulate rapid fibrosis can be used for further stabilization. Examples of such agents include fibrin sealants, tissue sealants, talc (dry or slurry), doxycycline, bleomycin, povidone iodine, minocycline, doxorubicin, streptokinase, urokinase, sodium tetradecyl sulfate, and/or silver nitrate. Other coatings to promote the stability of the implant 74 include calcium hydroxylapatite, aluminum oxide, bioactive hydroxyl apatite, or tricalcium phosphate. Such agents can be applied only at pre-selected locations on the implant 74, e.g., such as bottom and side boundaries, to leave easy access to the top portion of the implant 74 for removal. Alternatively, such agents can be injected directly into the flap 70 (or pocket), or may used to irrigate the flap 70 (or pocket), or may be placed within a gel or hydrogel in the flap 70 (or pocket).

Tissue adhesives, fibrin sealants, and glues such as cyanoacrylate, or cements such as polymethyl methacrylate (PMMA) cement can be applied to either improve stabilization or replace mechanical sutures or fasteners. A tissue ablation agent or energy source may be used to form avascular pockets.

Tissue ingrowth materials can also be used, as will be described in greater detail later.

b. Two Stage Flap Approach

The techniques described above can also be done in a two stage manner.

Figure 23A:
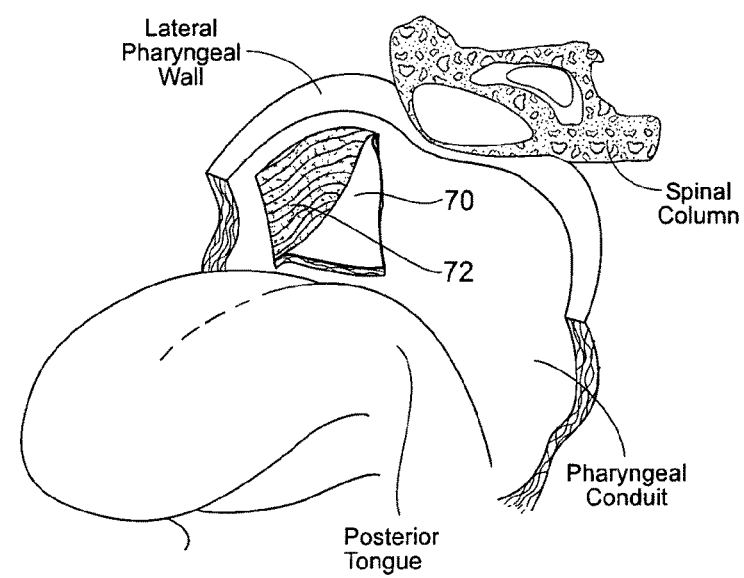
FIGS. 23A, 23B, and 23C are perspective anatomic views of a tongue and adjacent pharyngeal wall, simplified and diagrammatic, showing the formation of a surgical flap on a lateral pharyngeal wall and the implantation of the implant system shown in FIG. 22 in the flap.

In this arrangement (see FIG. 23A), pharyngeal flaps 70 (either lateral or posterior-lateral) and/or a tongue flap 70 can be formed in the manner just described, which can expose pharyngeal constrictor muscles 72 or genioglossal muscle 72, which can be fascial covered. FIG. 23A shows, for purpose of illustration, the flap being formed in a lateral pharyngeal wall. Alternatively, a surgical pocket can be formed.

Figure 22:
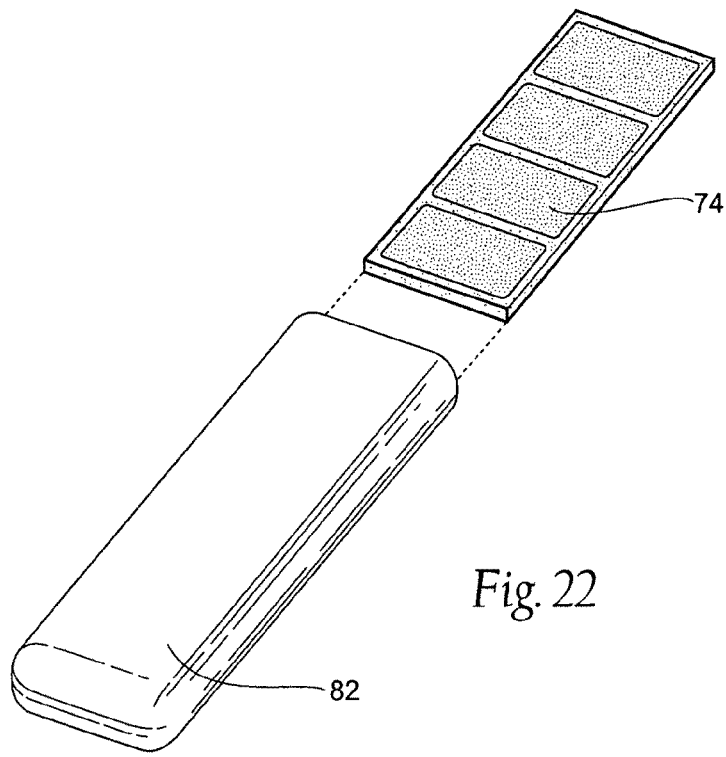
FIG. 22 is a perspective view of an implant system comprising a sleeve into which an implant can be inserted.
Figure 23B:
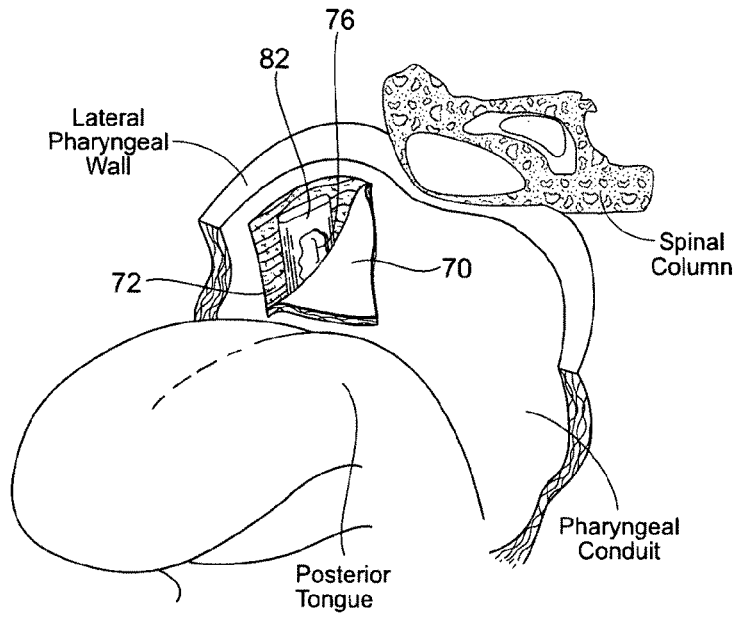

A modular receptacle 82 or sleeve (see FIG. 22) is then stabilized, e.g., within the muscosa, or against the fascia, or against or within muscle, in each flap 70 (see FIG. 23B) (or pocket), with resorbable or non-resorbable sutures, and/or staples, and/or hooks and/or fasteners, and/or darts, and/or clips, and/or screws, and/or adhesives, and/or glues such as cyanoacrylate, or cements such as polymethyl methacrylate (PMMA) cement. The flaps 70 (or pocket) are then closed with non-absorbable or absorbable suture 80, adhesives, or glues such as cyanoacrylate, or cements such as polymethyl methacrylate (PMMA) cement. Supplemental systemic antibiotics are desirably utilized.

Figure 23C:
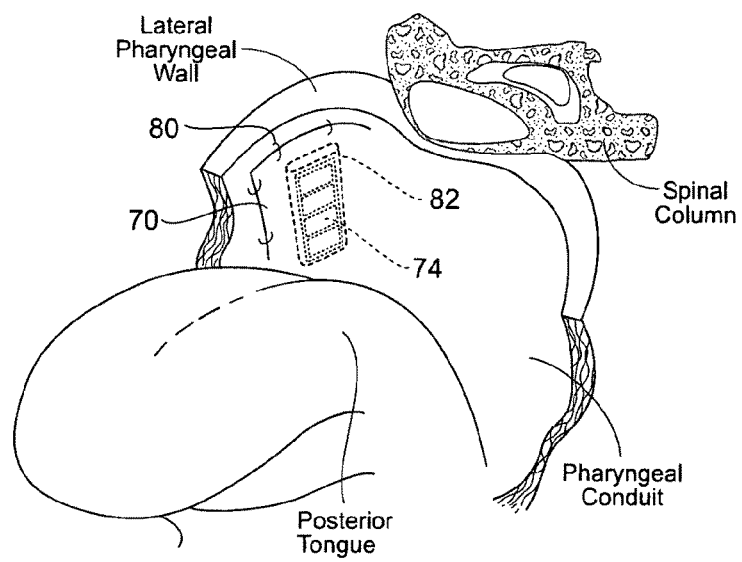

As FIG. 23C shows, the implanted receptacle 82 is allowed to stabilize within the flap or pocket by fibrous capsule formation or tissue ingrowth. To accelerate or enhance stabilization of the receptacle 82 in the flap 70 or pocket, as in the single stage approach, agents can be used to stimulate rapid fibrosis in tissue surfaces, and/or tissue sealants, adhesives, and/or glues can be applied to either improve stabilization or replace mechanical sutures or fasteners; and/or tissue ablation agents or energy sources can be applied to form avascular pockets, and/or tissue ingrowth materials can be used, as will be described in greater detail later.

After the receptacle 82 has been allowed to stabilize within the flap 70 (or pocket), a selected implant 74 is loaded into the receptacle 82 (see FIG. 23D). This can be done, e.g., by re-opening a portion of the flap or pocket, or the use of transmucosal trochars.

The two stage approach allows stabilization of a basic implant support (i.e., the receptacle 82) to occur within a flap or pocket prior to the introduction of the operative implant 74, e.g., one subject to magnetic forces or another potentially destabilizing force. The two stage approach also allows one to titrate, e.g., magnetic force requirements to the individual patient's needs without replacing the basic implant support.

C. Instrument Approaches

Implants of the types described herein, or of other designs and functions, can also be placed percutaneously into the pharyngeal wall and/or tongue (the locations shown in FIG. 2) or elsewhere in the body by use of percutaneous instrument systems 84, without opening a flap or another incision site. An instrument system 84 may be variously constructed.

Figure 26A:
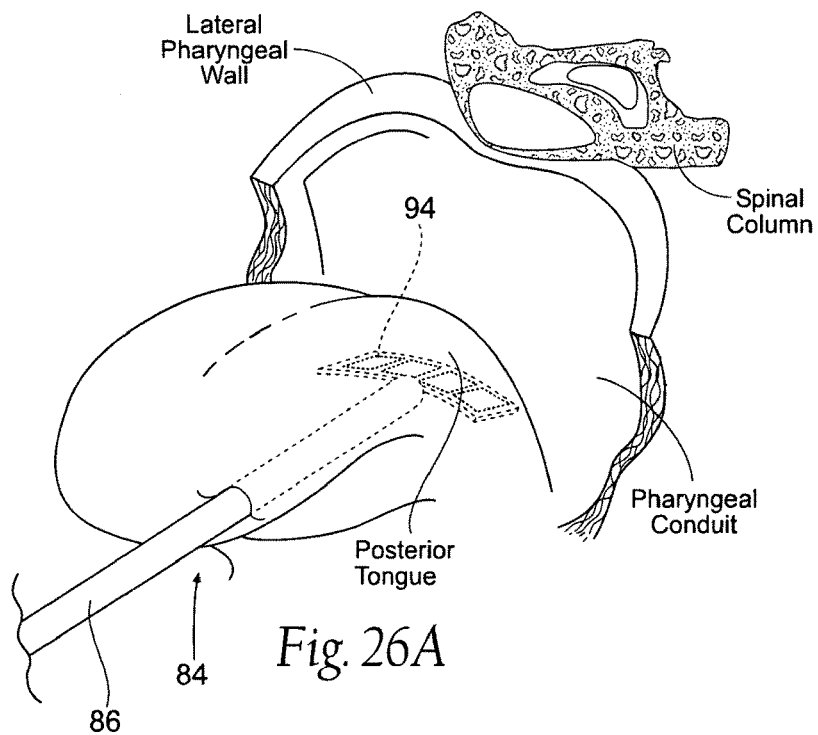
FIG. 26A is perspective anatomic view of a tongue and adjacent pharyngeal wall, simplified and diagrammatic, showing the use of the instrument system shown in FIGS. 24A to 24C to place an implant in a posterior tongue.

FIGS. 24A to 24C show a representative system 84. The system 84 includes an access cannula 86 which, in use, can be deployed within the oral cavity to create a percutaneous path to a selected implantation site either in a tongue (see FIG. 26A) or in a pharyngeal wall (see FIG. 26B). A trocar-tip guide wire 90 can be used to initially puncture the targeted tissue site. A cannulated tissue plane dissector 88 can then be passed over the guide wire 90 to create an entry site to the tissue and to separate the tissue layers at the implantation site. The guide wire 90 can then be removed, and the access cannula 86 can be passed over the dissector 88 to the implantation site. The dissector 88 and guide wire 90 are removed, to open a working channel through the access cannula 86 to the implantation site.

Alternatively, the dissector 88 and access cannula 86 can be deployed nested together, being passed as a unit into tissue, with or without use of a guide wire. The blunt tip of the dissector 88 projects beyond the distal end of the cannula 86, serving to open an entry site and separate the tissue layers at the implantation site. The dissector 88 can then be removed from the cannula 86, to open the working channel.

In either embodiment, another instrument may be deployed through the working channel of the cannula 86, if necessary, to create a surgical pocket in the tissues to receive the implant.

As FIG. 24B shows, the system 84 may include a implant delivery tool 92. The tool 92 carries an implant 94 in a pre-loaded condition within its distal end. The tool 92 is passed through the working channel of the cannula 86 to the implantation site. A plunger 96, or rod, abuts against the implant. By holding the plunger 96 stationary and pulling back upon the tool 92, the implant can be expelled from distal end of the tool 92 into the prepared implantation site (see FIG. 24C). The cannula 86 and the implant delivery tool 92 can, at the appropriate time, be removed as a unit, leaving the implant behind.

Alternatively, the implant 94 can be loaded directly into the proximal end of the cannula 86, and the plunger 96 passed through the cannula 86 to advance the implant to the distal tip of the cannula 86. Holding the plunger stationary and pulling back on the cannula 86 expels the implant into the prepared implantation site. The cannula 86 and plunger 96 can then be removed as a unit, leaving the implant behind.

As FIG. 24C shows, a given implant 94 may be rolled or folded within the working channel of the cannula 86 or within the delivery tool 92 during deployment. In this arrangement, the implant 94 can include a material that actively or passively reshapes the implant 94 into its in-use condition after deployment into the implantation site. For example, the material may urge the implant 94 toward a lay-flat or curvilinear in-use condition when free of the cannula 86. For example, the material may possess a spring constant or include a shape memory to self-expand to the desired lay-flat or curvilinear in-use condition. Alternative, the implant 94 may be deployed in conjunction with a shaping member that actively reshapes the implant 94 into it in-use condition after deployment from the cannula 86. For example, the implant 94 may be wrapped around an expandable structure that expands or inflates to force the implant to flatten. Alternatively, the implant 94 may be wrapped around a mechanically expanding member that transforms linear or rotational motion into motion that will lay out the implant 94.

Figure 25A:
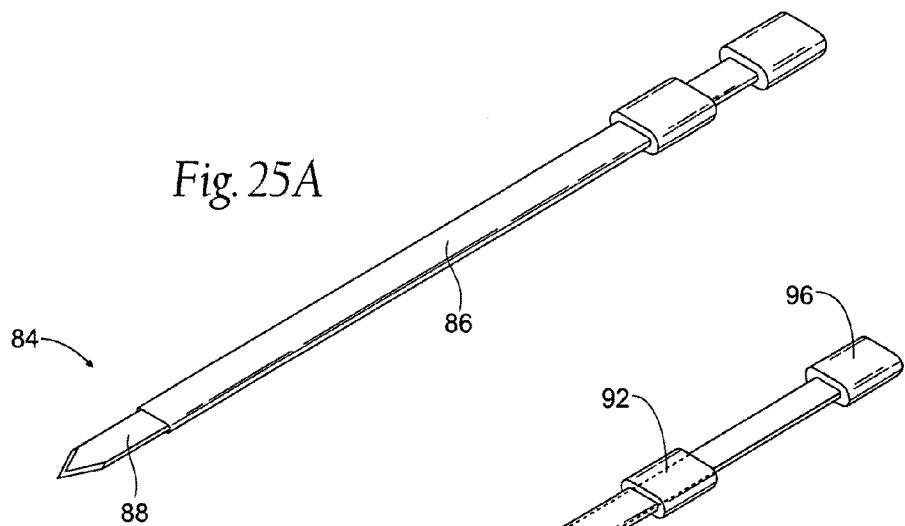
FIGS. 25A, 25B, and 25C show an instrument system for percutaneously implanting an implant comprising a rectilinear access cannula through which a correspondingly-shaped tissue dissection tool and implant delivery tool can be passed, FIG. 25A showing passage of the tissue dissection tool through the cannula, FIG. 25B showing the passage of the implant delivery tool through the cannula, and FIG. 25C showing the delivery of the implant by the implant delivery tool.
Figure 25B:
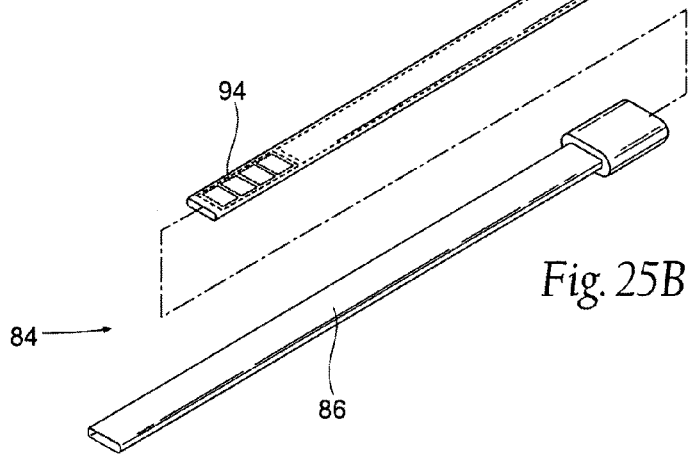
Figure 25C:
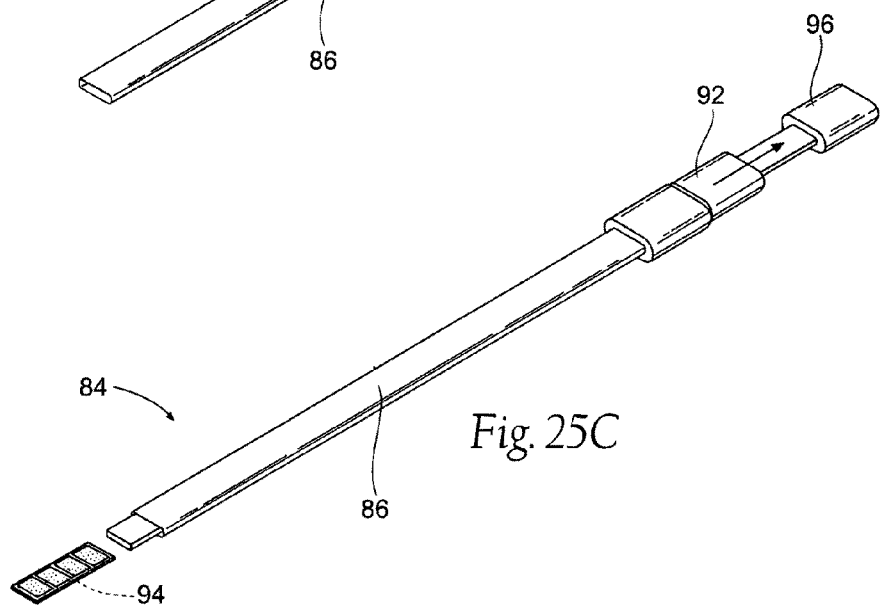

In FIGS. 24A to 24C, the cannula 86 is shown to be cylindrical in shape, and the other tools that pass through the working channel are correspondingly shaped. The shape can be cylindrical, oval, rectilinear, or other configurations. As FIGS. 25A and 25B show, the shape of the delivery tools may be customized to shape of the implant 94 itself. For example, when the implant 94 comprises a rectilinear shape, the working channel itself can be correspondingly rectilinear in cross section, as FIGS. 25A to 25C show.

For example, in this arrangement (see FIG. 25A), the rectangular cannula 86 and the rectangular dissector 88 form a combination tool 98, which can be manipulated to gain access to the tissues. The tool 98 nests the dissector 98 within the cannula 86. The dissector 98 takes the form of a sharp, inner stylet with a trocar or blade tip that can puncture the tissue. The cannula 86 takes the form of an outer stylus holding the dissector 98. The combination tool 98 punctures the tissue, after which the dissector 88 is withdrawn from the cannula 86. If it is necessary to form a pocket within the tissue, another blunt tip instrument may be passed through the working channel of the cannula 86 to further separate the tissue layers.

As shown in FIG. 25B, a rectangular implant 94 is loaded into a rectangular delivery tool 92. The delivery tool 92 is passed through the working channel of the cannula 86 to the site that has been prepared for implantation. A rectangular plunger 96 is advanced through the delivery tool 92 to expel the implant 94 from the tool 92 into the implantation site.

Once deployed, the implant 94 may or may not be further anchored to the underlying tissues/muscle layer. Within the implantation site, the position of the implant 94 may be stabilized using a suitable stabilization element, e.g., one or more staples, and/or clips, and/or darts, and/or sutures, and/or medical adhesives or glues, as previously described. Stablization can be achieved without fixation of the implant to mucosa or submucosa tissue, if desired. Tools that place the stabilizing element in the implant 94 may be an integrated part of the access cannula or implant delivery tool, or may comprise one or more separate tools that are themselves deployed through the working channel of the cannula 86, or may comprise one or more tools that are deployed by some other means.

The working channel of the cannula 86 can also be used to flush the delivery site with antibiotic solutions prior to, during, and after implant delivery. The antibiotic solutions can include, e.g., chlorohexalin, kanamicin, Baytril, cephalexin, or gentamicin.

Figure 26B:
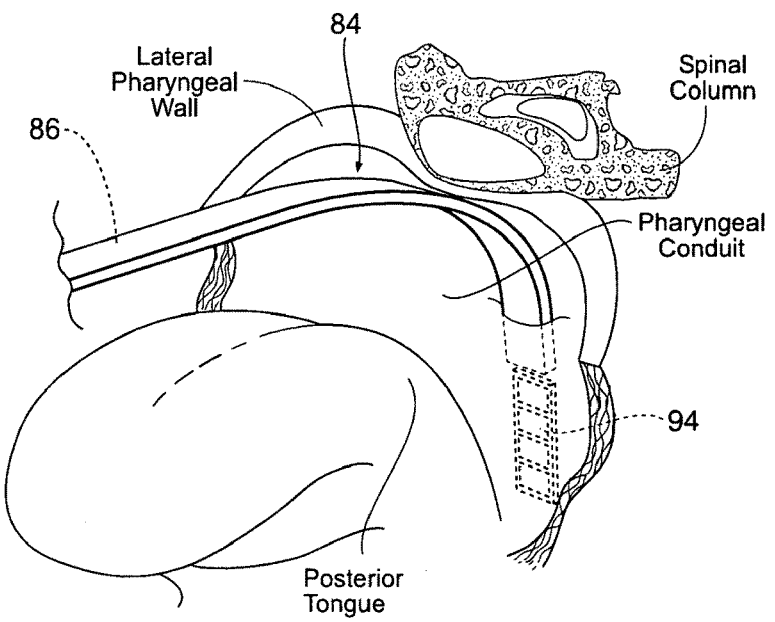
FIG. 26B is perspective anatomic view of a tongue and adjacent pharyngeal wall, simplified and diagrammatic, showing the use of the instrument system shown in FIGS. 25A to 25C to place an implant in a lateral pharyngeal wall.

The cannula and other tools of the system can be made of metal, plastic, or ceramic materials, or combinations thereof. The cannula and other tools can be made of flexible materials, allowing the instruments to be flexed or shaped during use (as FIG. 26B shows for purposes of illustration).

As shown in FIG. 30A, the implant 94 can carry integrated stabilization elements 100 that automatically anchor the implant to tissue when it is released into the implantation site. Stabilization elements 100 can be integrated to the implant in various ways. For example, as shown in FIG. 30A, the tissue stabilization elements 100 are carried at the end of elastic arms 102 and 104, having spring-like characteristics. The elastic arms 102 and 104 are secured at opposite ends of the implant 94, and they occupy different planes. The elastic arms 102 are secured along the front surface of the implant 94, and the elastic arms 104 are secured along the rear surface of the implant 94. This arrangement balances the stabilizing forces about the implant 94, as well as facilitates the deployment of the elements 100 in the first instance. The elastic arms 102 and 104 may be made of shape memory plastic or metallic materials that expand within the plane of the implant 94 or outside the plane of the implant 94.

The elastic arms 102 and 104 are placed into compression and bent inward toward the implant 94, into what can be called an inboard condition, when the implant 24 is confined within the delivery tool 92 (see FIG. 30C). When free of the confines of the delivery tool 92 (see FIGS. 30A and 30D), the arms 102 and 104 spring outward from the implant 94, due to their spring-like characteristics, into what can be called an outboard condition, engaging tissue.

In this arrangement (see FIG. 30B), the distal end of the delivery tool 92 includes opposing slots 106 that align with the elastic arms 102 on the trailing edge of the implant 94 (i.e., the edge that is last to exit the tool 92 during implant deployment). The elastic arms 104 on the leading edge of the implant 94 (i.e., the edge that is first to exit the tool 92 during implant deployment) do not align with the slots 106.

The implant 94 is loaded into the tool 92, trailing edge first, with the elastic arms 102 and 104 in their outboard condition. The slots 106 accommodate passage of the elastic arms 102 on the trailing edge of the implant 94, as the implant 94 is progressively loaded into the tool 92. As FIG. 30B best shows, the elastic arms 102 on the trailing edge of the implant 94 will abut the terminus 108 of the slots 106 about the same time as the leading edge of the implant 94 abuts the distal terminus 110 of the tool 92. Loading the implant 94 further into the tool 92 results in resiliently bending the elastic arms 102 and 104 progressively forward into their inboard condition. The slot terminus 108 will deflect the elastic arms 102 forward into compression, and the end terminus 110 will deflect the elastic arms 104 forward into compression. When fully loaded within the tool 92, the walls of the tool 92 keep the elastic arms 102 and 104 in compression in their inboard condition.

At time of deployment, the plunger 96 is held stationary, and the tool 92 is drawn away from the implantation site. This will release the implant 92 from the confines of the tool 92, leading edge first. As the leading edge of the implant clears the tool 92, the arms 104 will spring outward to their outboard condition (see FIG. 30D). As the trailing edge of the implant clears the tool 92 (as FIG. 30A shows), the arms 102 will spring outward to their outboard condition. The self-deployed stabilization elements 100 anchor the implant 94 in adjacent tissue, without need for deployment of a separate stabilization tool.

Figure 27A:
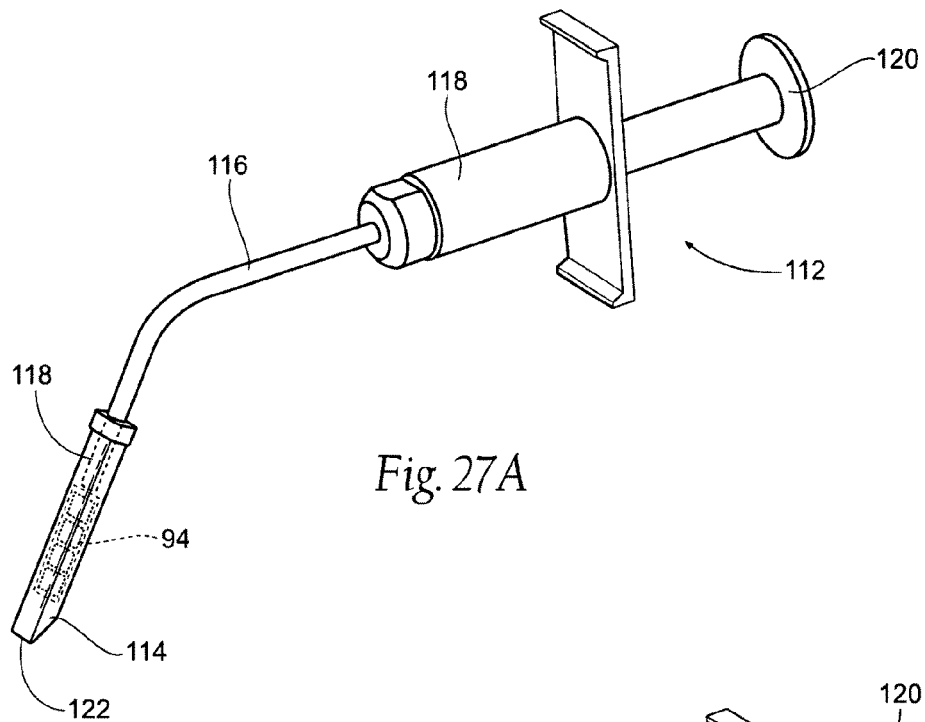
FIGS. 27A and 27B are perspective side views of an alternative embodiment of an instrument system for percutaneously implanting an implant, the system including a syringe-like remote actuator to expel an implant from a needle-cannula carried at the distal end of a flexible tube.
Figure 27B:
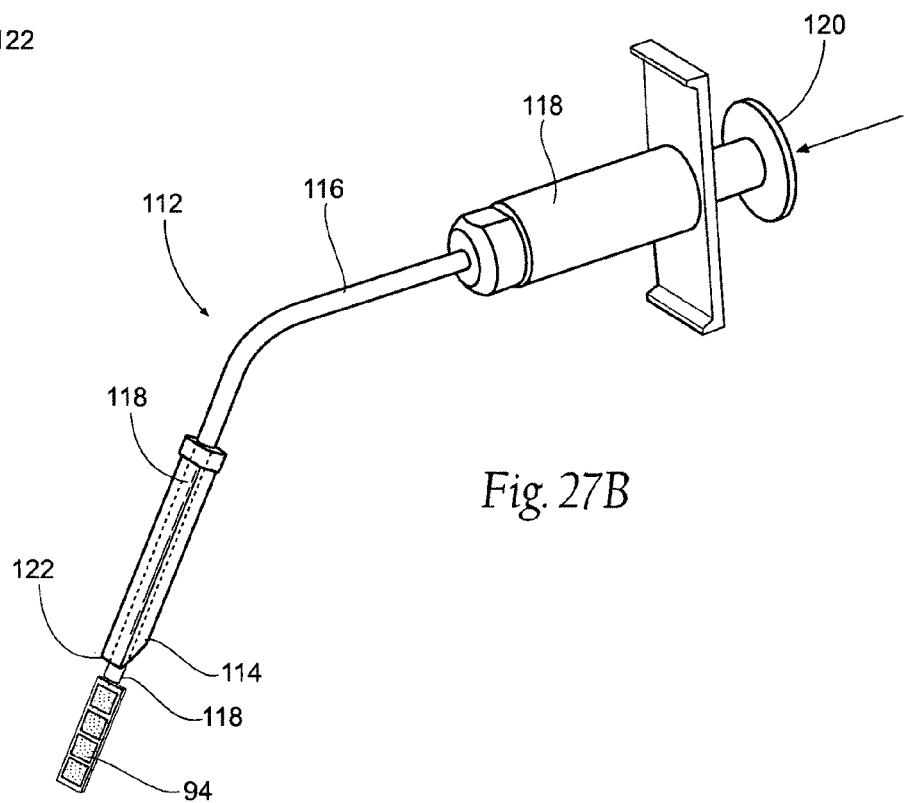

Other systems and devices may be used to deliver an implant to an implantation site in the pharyngeal conduit or elsewhere in the body. For example, FIGS. 27A and 27B show a hand-held tool 112 comprising a delivery cannula 114 coupled by a flexible tubing 116 to a handle 118. An implant 94 is carried within the cannula 114. The cannula 114 includes a needle-like, tissue penetrating distal tip 122. The distal tip 122 can be placed into tissue in the tongue or pharyngeal wall, while the handle 118 remains fully or partially inside the oral cavity.

A plunger 118 abuts against the trailing edge of the implant 94. The plunger 118 is coupled by a push-pull cable (which passes through the tubing 116) to an actuator 120 on the handle 114. Pushing forward on the actuator 120 advances the plunger 118 (see FIG. 27B), which expels the implant from the cannula 114 into the implantation site.

Figure 28A:
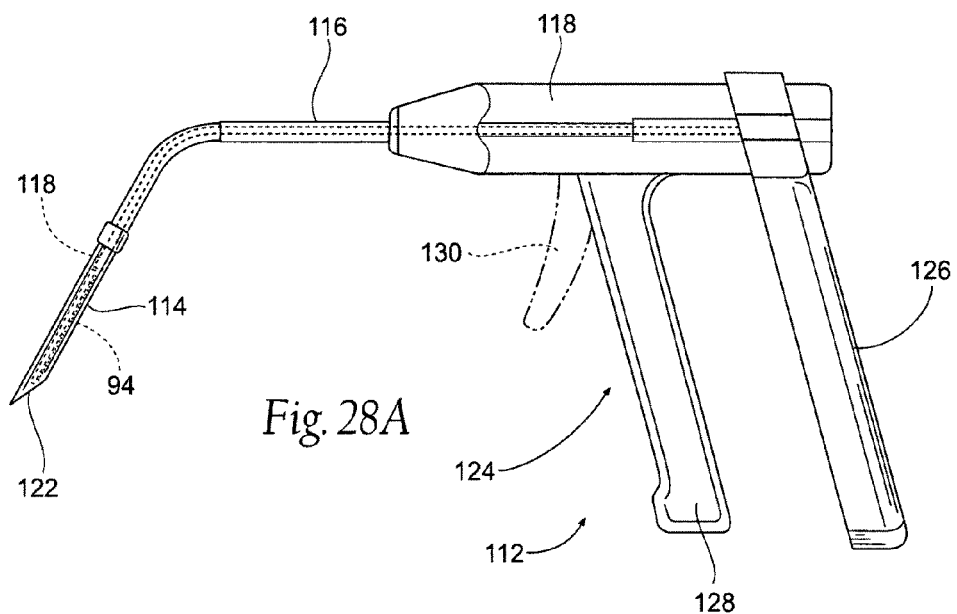
FIGS. 28A and 28B are perspective side views of an alternative embodiment of an instrument system for percutaneously implanting an implant, the system including a trigger-like remote actuator to expel an implant from a needle-cannula carried at the distal end of a flexible tube.
Figure 28B:
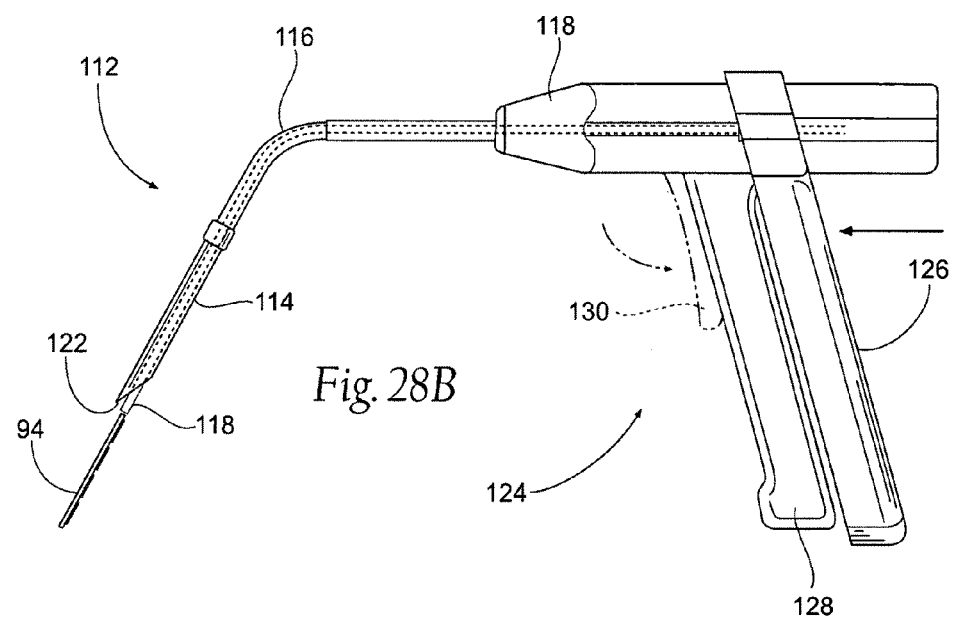
Figure 29A:
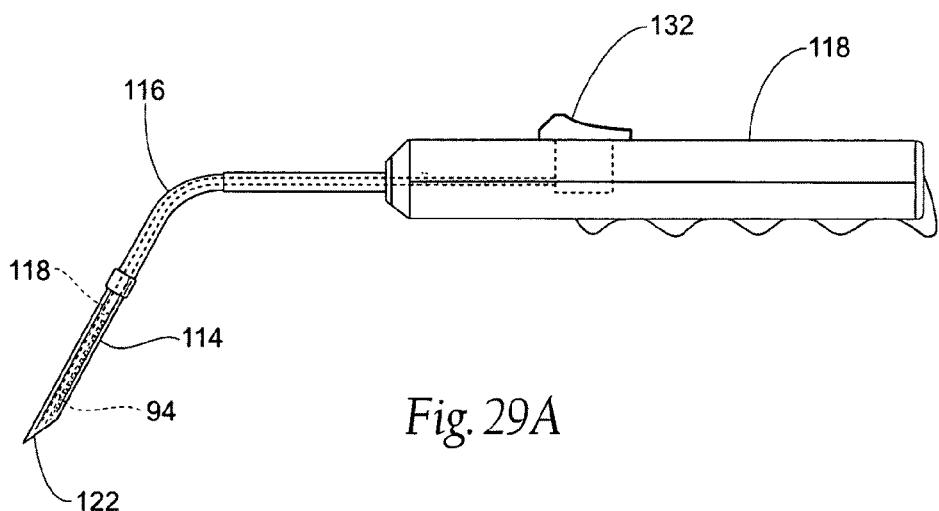
FIGS. 29A and 29B are perspective side views of an alternative embodiment of an instrument system for percutaneously implanting an implant, the system including a sliding remote actuator to expel an implant from a needle-cannula carried at the distal end of a flexible tube.
Figure 29B:
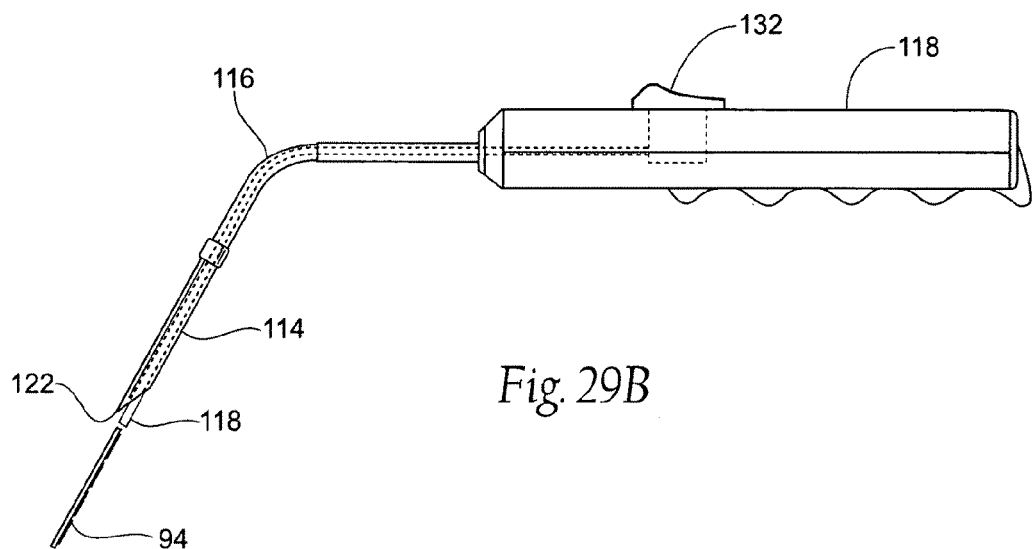

In the alternative embodiment shown in FIGS. 28A and 28B, the actuator 120 takes the form of a trigger mechanism 124, which can be actuated by squeezing a slidable aft trigger member 126 toward a stationary forward handle 128, or by pulling a pivot trigger 130 (shown in phantom lines) toward the handle 128. In the alternative embodiment shown in FIGS. 29A and 29B, the actuator 120 takes the form of a sliding thumb lever 132.

D. Tissue In-Growth Surfaces

In addition to any of the just-described tissue fixation methodologies, a given implant can include a tissue in-growth surface 70 (see FIG. 2). The use of such surfaces 70 has previously been described in association with the polymer-bonded, hybrid, and layered magnetic structures.

In general, the surface 70 provides an environment that encourages the in-growth of neighboring tissue on the implanted structure. Tissue in-growth is defined as the filing of pores in an implanted material with cellular material. As in-growth occurs, the implanted structure 12 will become securely anchored, resisting migration or extrusion from the tissue. The tissue in-growth surface 70 thus enhances tissue adhesion and stabilization, and thereby further stabilizes and fixes the position of the implanted structure 12 in the targeted implantation site.

The tissue in-growth surface 70 can be formed in various ways, such as the porous nature of the material, knitting, weaving, through holes, or molding a porous structure or surface. Examples of suitable materials include polytetrafluoroethylene (PTFE), expanded PTFE, polyethylene terephthalate such as Dacron® (PET) fabric, other permanent polyesters, polyurethane, silicone, polypropylenepolyvinyl alcohol, biodegradeable polyesters such as polylactic acid and polyglycolic acid.

It may be desirable to mechanically anchor the implanted magnetic structures while allowing in-growth to occur. Anchoring may be accomplished by use of resorbable or non-resorbable sutures, screws or other mechanical fasteners made of resorbable or non-resorbable materials such as polyglycolic acid or other similar compounds. Tissue adhesives and/or tissue cements such as PMMA and/or tissue sealants, and/or tissue glue such as cyanacrylate may also be used to provide tissue adhesion, fixation, and stabilization.

Complete tissue in-growth is determined by the percentage of the material that has been infiltrated by the cellular material. With pore sizes from 100 micrometers to 500 micrometers, blood vessels can be formed. With pore sizes of 10 micrometers to 100 micrometers, cells to small capillaries can form.

Also, materials or shapes may be used that encourage tissue or fibrotic encapsulation of the implant 94, with or without tissue ingrowth.

III. Systems for Providing Treatment

It is apparent from the foregoing that various systems can be created, based upon the above-described implant structures, implantation devices, and surgical implantation techniques, to make it possible for healthcare providers to treat physiologic conditions with enhanced effectiveness.

Figure 31:
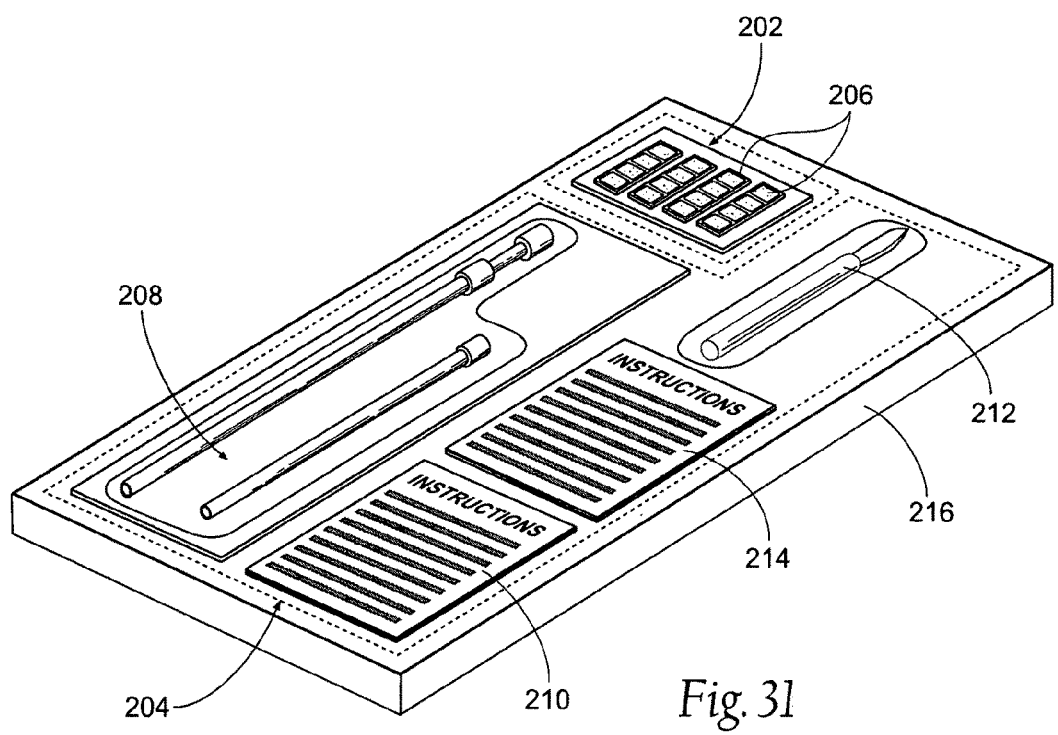
FIG. 31 is a perspective view of an integrated system in kit form that includes an implant component and an implantation component, which make possible the treatment of physiologic conditions, e.g., dysfunctions affecting the pharyngeal conduit, such as sleep disordered breathing, snoring, or sleep apnea.

For example, as shown in FIG. 31, one can make available a system 200 that can provide treatment for dysfunctions affecting the pharyngeal conduit, such as sleep disordered breathing, snoring, or sleep apnea. In one desired embodiment, the system 200 would have an implant component 202 and an implantation component 204.

The implant component 202 can include providing one or more implants 206 that are sized and configured to be implanted in a targeted tissue region comprising at least one pharyngeal structure or at least one anatomic component within a pharyngeal conduit. Several embodiments of implants 206 having this characteristic have been described herein. Other representative embodiments are described in U.S. patent application Ser. No. 10/718,254, filed Nov. 20, 2003 and entitled "Devices, Systems, and Methods to Fixate Tissue Within the Regions of the Body, Such as the Pharyngeal Conduit"; U.S. patent application Ser. No. 10/656,861, filed Sep. 6, 2003 and entitled "Magnetic Force Devices, Systems, and Methods for Resisting Tissue Collapse within the Pharaygeal Conduit"; U.S. patent application Ser. No. 10/236,455, filed Sep. 6, 2002 and entitled "Systems and Methods for Moving and/or Restraining Tissue in the Upper Respiratory System"; and U.S. Provisional Patent Application Ser. No. 60/441,639, filed Jan. 22, 2003 and entitled "Magnetic Splint Device and Method for the Treatment of Upper Airway Collapse in Obstructive Sleep Apnea;" and U.S. Provisional Patent Application Ser. No. 60/456,164, filed Mar. 20, 2003 and entitled "Device and Method for Treatment of Sleep Related Breathing Disorders Including Snoring and Sleep Apnea," which have been incorporated herein by reference.

The system 200 desirably includes an implantation component 204, because of challenges that are presented in the placement of implants 206 in the dynamic tissue environment of the pharyngeal conduit. The implantation component 204 includes providing at least one tool 208 and/or instructions 210 for placing the implant 206 in a tissue region, e.g., through a percutaneous access path, using the tools described herein and shown in FIGS. 24 to 30; or by forming a surgical flap as described herein and shown in FIGS. 19 to 23; or by forming a surgical pocket, as also described herein.

The implantation component 204 can also include providing at least one tool 212 and/or instructions 214 for stabilizing the implant within a mucosa, or a submucosa, or against a fascia, or against or within a muscle, as described herein. Alternatively, the tool 212 and/or instructions 214 can make possible the stabilization of the implant against submucosa, or a fascia, or against or within a muscle, without stabilizing through a mucosa, as described herein. Other tools and instructions can be provided, e.g., to make various mechanical fixation materials (as described herein) accessible; or to make agents that stimulate rapid fibrosis (as described herein) available; or to provide antibiotic materials (as described herein).

The basic components 202 and 204 of the system 200 can be provided individually, or packaged in the form of a kit 216, as FIG. 31 shows. The various instructions can be in written form, electronic form, or verbal form, which can be provided in the kit 216 and/or as part of a training program or web site for clinicians.

The above-described embodiments of this invention are merely descriptive of its principles and are not to be limited. The scope of this invention instead shall be determined from the scope of the following claims, including their equivalents.

What is claimed is:

1. An implant comprising a generally planar structure sized and configured to occupy a targeted tissue region in an oral cavity the structure comprising a rectilinear shape including a first end, a second end disposed opposite and distal from the first end, opposing sides, and first and second arms each being carried by the first and second ends of the structure, each of the arms being sized and configured to be selectively deployed to extend laterally outward from the opposing sides of the rectilinear structure into contact with tissue, thereby anchoring the implant in the tissue.

2. An implant according to claim 1 wherein each of the arms is deflectable between an inboard condition extending generally along the structure and an outboard condition extending outward of the structure in contact with tissue.

3. An implant according to claim 2 wherein the arms comprises an elastic material.

4. An implant according to claim 2 wherein the arms comprises a shape memory material.

5. An implant according to claim 2, wherein the arms comprise a material having a spring-like mechanical property.

6. An implant according to claim 2 wherein the arms are resiliently biased toward the outboard condition.

7. An implant according to claim 1 wherein the arms are resiliently biased toward a deployed condition outward of the structure.

8. An implant according to claim 7 wherein the arms are resiliently movable within a delivery tool toward an inboard condition generally along the structure.

9. An implant according to claim 8 wherein the arms resiliently return toward the deployed condition upon release from the delivery tool.

10. An implant according to claim 1 wherein the arms are sized and configured to be selectively deployed outward of the structure into contact with a mucosa, or a submucosa, or against a fascia, or against or within a muscle.

11. An implant according to claim 1 wherein the arms are sized and configured to be selectively deployed outward of the structure against a submucosa, or fascia, or against or within a muscle, without stabilizing through a mucosa.

12. An implant according to claim 1 wherein arms anchor the structure in tissue.

13. An implant according to claim 1 wherein the arms fixate the structure in tissue.

14. An implant system comprising a generally planar implant sized and configured to occupy a targeted tissue region in an oral cavity, the implant comprising a rectilinear shape including a first end, a second end disposed opposite and distal from the first end, opposing sides, and first and second arms being carried by the first and second ends of the implant, the arms being deflectable between an inboard condition extending generally along the rectilinear implant and an outboard condition extending laterally outward from the opposing sides of the rectilinear implant in contact with tissue, the arms being resiliently biased toward the outboard condition, and a delivery tool sized and configured to hold the implant and deflect the arms toward the inboard condition for delivery to the targeted tissue region and to selectively release the implant within the targeted tissue region to free the arms to resiliently deflect toward the outboard condition in contact with tissue.

15. A method comprising providing a generally planar implant sized and configured to occupy a targeted tissue region in an oral cavity, the implant comprising a rectilinear shape including a first end, a second end disposed opposite and distal from the first end, opposing sides, and first and second arms being carried by the first and second ends of the implant, the arms being deflectable between an inboard condition extending generally along the rectilinear implant and an outboard condition extending laterally outward from opposing sides of the rectilinear implant in contact with tissue, the arms being resiliently biased toward the outboard condition, delivering the implant to a targeted tissue region in an oral cavity with the arms deflected toward the inboard condition, and allowing the arms to resiliently deflect toward the outboard condition in contact with tissue in the tissue region.

16. A method according to claim 15 wherein the arms, when deflected in the outboard condition, anchors the implant in tissue.

17. An implant method according to claim 15 wherein the arms, when deflected in the outboard condition, fixates the implant in tissue.

18. A method according to claim 17 wherein the arms, when deflected in the outboard condition, are deployed outward of the implant in contact with a mucosa, or a submucosa, or against a fascia, or against or within a muscle.

19. A method according to claim 17 wherein the arms, when deflected in the outboard condition, are deployed outward of the implant against a submucosa, or fascia, or against or within a muscle, without stabilizing through a mucosa.

20. A method according to claim 17 further including stabilizing a desired orientation of the tissue region by providing the implant, delivering the implant, and allowing the arms to resiliently deflect toward the outboard condition to stabilize the implant in the tissue region.

21. A method according to claim 20 wherein stabilizing a desired orientation of the tissue region treats sleep disordered breathing.

* * * * *